US007442513B2

(12) United States Patent
Worley

(10) Patent No.: US 7,442,513 B2
(45) Date of Patent: Oct. 28, 2008

(54) METHOD OF SCREENING FOR AGENTS THAT MODULATE A HOMER SIGNALING PATHWAY

(75) Inventor: Paul F. Worley, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

(21) Appl. No.: 10/518,941

(22) PCT Filed: Jun. 18, 2003

(86) PCT No.: PCT/US03/19499

§ 371 (c)(1),
(2), (4) Date: Nov. 21, 2005

(87) PCT Pub. No.: WO2005/007844

PCT Pub. Date: Jan. 27, 2005

(65) Prior Publication Data

US 2006/0147914 A1  Jul. 6, 2006

(51) Int. Cl.
*G01N 33/53* (2006.01)
(52) U.S. Cl. ............................................. 435/7.1; 435/4
(58) Field of Classification Search ...................... None
See application file for complete search history.

(56) References Cited

U.S. PATENT DOCUMENTS

| 6,294,355 | B1 | 9/2001 | Worley et al. | ............... | 435/69.1 |
| 6,720,175 | B1 | 4/2004 | Worley et al. | ............ | 435/252.3 |
| 2003/0027147 | A1 | 2/2003 | Worley et al. | ................ | 435/7.1 |

OTHER PUBLICATIONS

Xiao et al. Current Opinion in Neurobiology 2000;10:370-374.*
Heitman et al. Molecular Cellular Biology 1993;13(8):5010-5019.*
Bartolomeis et al., "Acute Administration of Antipsychotic Modulates Homer Striatal Gene Expression Differentially," *Molecular Brian Research*, vol. 98, pp. 124-129, (2003).
Beneken et al., "Structure of the Homer EVH1 Domain-Peptide Complex Reveals a New Twist in Polyproline Recognition," *Neuron*, vol. 26, pp. 143-154, (2000).
Brakeman et al., "Homer: A Protein that Selectively Binds Metabotropic Glutamate Receptors," Nature, vol. 386, pp. 284-288, (1997).
Brecht et al., "Changes in Peptidyl-Proyl CIS/TRANS Isomerase Activity and FK506 Binding Protein Expression Following Neuroprotection by FK506 in the Ischemic Rat Brain," *Neuroscience*, vol. 120, pp. 1037-1048, (2003).
Brown et al., "A Mammalian Protein Targeted by G1-Arresting Rapamycin-Receptor Complex," *Nature*, vol. 369, pp. 756-758, (1994).
Clipstone and Crabtree, "Identification of Calcineurin as a Key Signalling Enzyme in T-Lymphocyte Activation," *Nature*, vol. 357, pp. 695-697, (1992).
Feng et al., "Homer Regulates Gain of Ryanodine Receptor Type 1 Channel Complex," *J Biol Chem*, vol. 277, pp. 44722-44730, (2002).

Fesik et al., "Isotope-Edited NMR of Cyclosporin A Bound to Cyclophilin: Evidence for a *Trans* 9,10 Amide Bond,," *Science*, vol. 250, pp. 1406-1409, (1990).
Fischer et al., "Cyclophilin and Peptidyl-Prolyl *Cis-Trans* Isomerase are probably identical Proteins," *Nature*, vol. 337, pp. 476-478, (1989).
Fruman et al., "Immunophilins in Protein Folding and Immunosuppression," *FASEB J*, vol. 8, pp. 391-400, (1994).
Goel et al., "Regulation of Drosophila TRPL Channels by Immunophilin FKBP59*," *J Biol Chem*, vol. 276, pp. 38762-38773, (2001).
Goethel and Marahiel, "Peptidyl-Prolyl *Cis-Trans* Isomerases, a Superfamily of ubiquitous folding Catalysts," *Cell Mol Life Sci*, vol. 55, pp. 423-436, (1999).
Guo et al., "Neuroimmunophilins: Novel Neuroprotective and Neuroregenerative Targets," *Ann Neurol*, vol. 50, pp. 6-16, (2001).
Harding et al., "A Receptor for the Immuno-Suppressant FK506 is a *Cis-Trans* Peptidyl-Prolyl Isomerase," *Nature*, vol. 341, pp. 758-760, (1989).
Kammermeier et al., "Homer Proteins Regulate Coupling of Group I Metabotropic Glutamate Receptors to N-Type Calcium and M-Type Potassium Channels," *J Neurosci*, vol. 20, pp. 7238-7245, (2000).
Kofron et al., "Determination of Kinetic Constants for Peptidyl Prolyl Cis-Trans Isomerases by an Improved Spectrophotometric Assay," *Biochemistry*, vol. 30, pp. 6127-6134, (1991).
Kunz and Hall, "Cyclosporin A, FK506 and Rapamycin: More than just Immunosuppression," *Trends Biochem Sci*, vol. 18, pp. 334-338, (1993).
Liu et al., "Calcineurin is a Common Target of Cyclophilin-Cyclosporin A and FKBP-FK506 Complexes," *Cell*, vol. 66, pp. 807-815, (1991).
Liu et al., "Inhibition of T Cell Signaling by Immunophilin-Ligand Complexes Correlates with Loss of Calcineurin Phosphatase Activity," *Biochemistry*, vol. 31, pp. 3896-3901, (1992).
Lu et al., "A Human Peptidyl-Prolyl Isomerase Essential for Regulation of Mitosis," *Nature*, vol. 380, pp. 544-547, (1996).
O'Keefe et al., "FK506 and CsA-Sensitive Activation of the Interleukin-2 Promoter by Calcineurin," *Nature*, vol. 357, pp. 692-694, (1992).
Sabatini et al., "RAFT1: A Mammalian Protein that binds to FKBP12 in a Rapamycin-Dependent Fashion and is Homologous to Yeast TORs," *Cell*, vol. 78, pp. 35-43, (1994).
Snyder et al., "Immunophilins in the Nervous System," *Neuron*, vol. 21, pp. 283-294, (1998).
Snyder et al., "Neural Actions of Immunophilin Ligands," *Trends Pharmacol Sci*, vol. 19, pp. 21-26, (1998).

(Continued)

*Primary Examiner*—Jon P Weber
*Assistant Examiner*—Bin Shen
(74) *Attorney, Agent, or Firm*—DLA Piper LLP (US)

(57) ABSTRACT

The invention features a method of identifying, evaluating and screening for compounds or agents for the treatment of disorders involving the Homer signaling pathway in the modulation of immunosupression and neuroprotection. The method includes evaluating the ability of agents to modulate Homer protein activity, Homer protein/immunophilin-peptidylproline cis-trans isomerase interaction, and/or Homer protein/proline-type Homer ligand consensus sequence interaction to identify agents for such treatment. The invention also discloses treatment modalities involving agents identified by such methods.

30 Claims, 19 Drawing Sheets

OTHER PUBLICATIONS

Steiner et al., "Neurotrophic Actions of Nonimmunosuppressive Analogues of Immunosuppressive Drugs FK506, Rapamycin and Cyclosporin A," *Nat Med*, vol. 3, pp. 421-428, (1997).

Tu et al., "Homer Binds a Novel Proline-Rich Motif and Links Group 1 Metabotropic Glutamate Receptors with IP3 Receptors," *Neuron*, vol. 21, pp. 717-726, (1998).

Tu et al., "Coupling of mGluR/Homer and PSD-95 Complexes by the Shank Family of Postsynaptic Density Problems," *Neuron*, vol. 23, pp. 583-592, (1999).

Van Duyne et al., "Atomic Structure of FKBP-FK506, an Immunophilin-Immunosuppressant Complex," *Science*, vol. 252, pp. 839-842, (1991).

Xiao et al., "Homer Regulates the Association of Group 1 Metabotropic Glutamate Receptors with Multivalent Complexes of Homer-Related , Synaptic Proteins," *Neuron*, vol. 21, pp. 707-716, (2000).

Xiao et al., "Homer: A Link between Neural Activity and Glutamate Receptor Function," *Curr Opin Neurobiol*, vol. 10, pp. 370-374, (2000).

Zhou et al., "Phosphorylation-Dependent Prolyl Isomerization: A Novel Signaling Regulatory Mechanism," *Cell Mol Life Sci*, vol. 56, pp. 788-806, (1999).

* cited by examiner

Effect of FK-506 on mGluR5 Binding to Homer
*Time Course* mGluR5-transfected 293 Cells

1 μM FK-506 Drug Time (in vivo)

Homer3-GST
224 —
122 —

Offered
224 —

IB: α-HA ab (mGluR5)

Buffer:
1% TX-100
Calyculin A
NaF, NaPyrophosphate, NaVO3
Protease Inhibitor

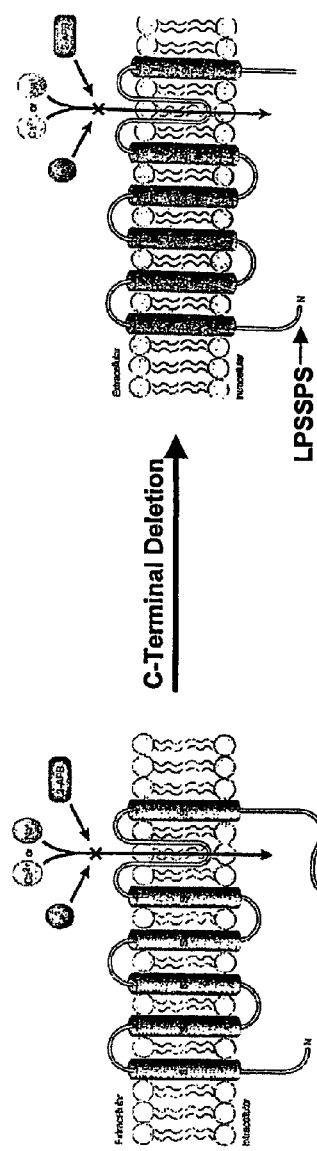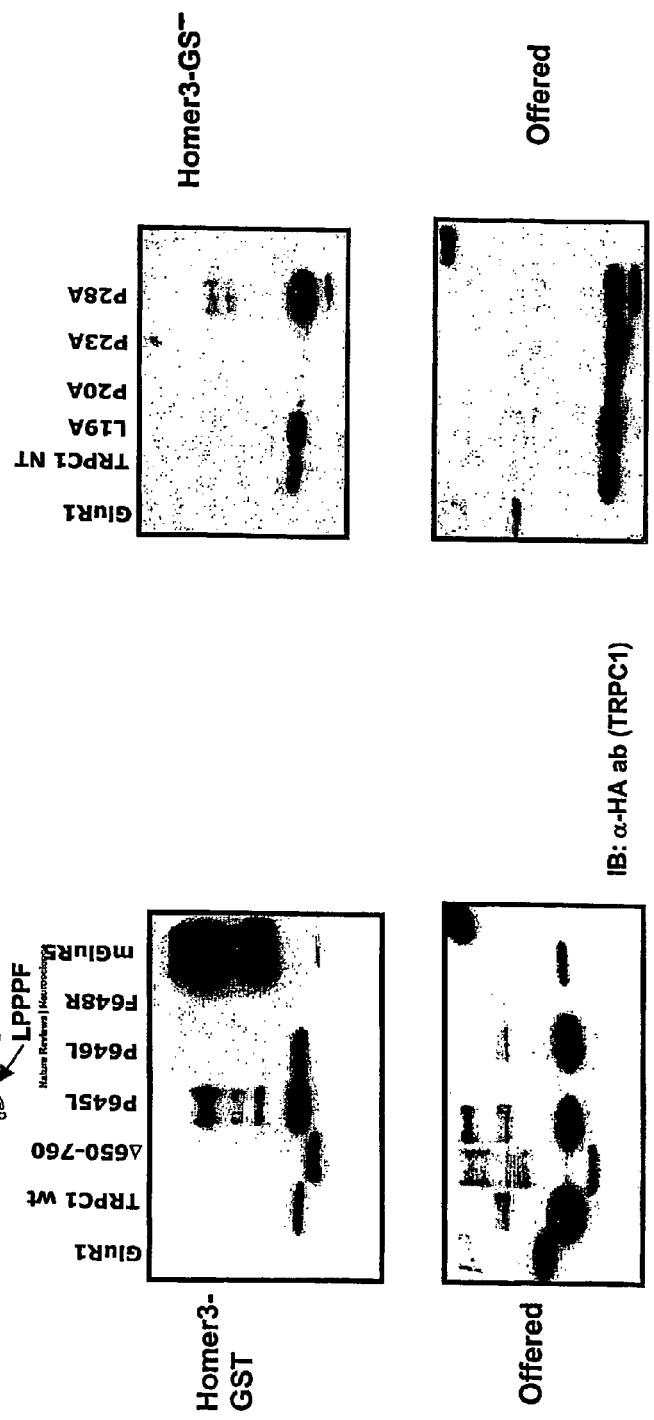
FIGURE 12

```
atg ggg gaa caa cct atc ttc agc act cga gct cat gtc ttc cag atc
gac cca aac aca aag aag aac tgg gta ccc acc agc aag cat gca gtt
act gtg tct tat ttc tat gac agc aca agg aat gtg tat agg ata atc
agt cta gac ggc tca aag gca ata ata aat agc acc atc act cca aac
atg aca ttt act aaa aca tct caa aag ttt ggc caa tgg gct gat agc
cgg gca aac act gtt tat gga ctg gga ttc tcc tct gag cat cat ctc
tca aaa ttt gca gaa aag ttt cag gaa ttt aaa gaa gct gct cgg ctg
gca aag gag aag tcg cag gag aag atg gaa ctg acc agt acc cct tca
cag gaa tca gca gga gga gat ctt cag tct cct tta aca cca gaa agt
atc aat ggg aca gat gat gag aga aca ccc gat gtg aca cag aac tca
gag cca agg gct gag cca gct cag aat gca ttg cca ttt tca cat agg
tac aca ttc aat tca gca atc atg att aaa    (SEQ ID NO: 6)
```

Figure 18

```
Met Gly Glu Gln Pro Ile Phe Ser Thr Arg Ala His Val Phe Gln Ile
Asp Pro Asn Thr Lys Lys Asn Trp Val Pro Thr Ser Lys His Ala Val
Thr Val Ser Tyr Phe Tyr Asp Ser Thr Arg Asn Val Tyr Arg Ile Ile
Ser Leu Asp Gly Ser Lys Ala Ile Ile Asn Ser Thr Ile Thr Pro Asn
Met Thr Phe Thr Lys Thr Ser Gln Lys Phe Gly Gln Trp Ala Asp Ser
Arg Ala Asn Thr Val Tyr Gly Leu Gly Phe Ser Ser Glu His His Leu
Ser Lys Phe Ala Glu Lys Phe Gln Glu Phe Lys Glu Ala Ala Arg Leu
Ala Lys Glu Lys Ser Gln Glu Lys Met Glu Leu Thr Ser Thr Pro Ser
Gln Glu Ser Ala Gly Gly Asp Leu Gln Ser Pro Leu Thr Pro Glu Ser
Ile Asn Gly Thr Asp Asp Glu Arg Thr Pro Asp Val Thr Gln Asn Ser
Glu Pro Arg Ala Glu Pro Ala Gln Asn Ala Leu Pro Phe Ser His Arg
Tyr Thr Phe Asn Ser Ala Ile Met Ile Lys  (SEQ ID NO: 7)
```

Figure 19

SEQUENCE LISTING

<160> NUMBER OF SEQ ID NOS: 30

<210> SEQ ID NO 1
<211> LENGTH: 5
<212> TYPE: PRT
<213> ORGANISM: Artificial sequence
<220> FEATURE:
<223> OTHER INFORMATION: Synthetic construct
<220> FEATURE:
<221> NAME/KEY: misc_feature
<222> LOCATION: (3)..(4)
<223> OTHER INFORMATION: Xaa can be any naturally occurring amino acid

<400> SEQUENCE: 1

Pro Pro Xaa Xaa Phe
1               5

<210> SEQ ID NO 2
<211> LENGTH: 6
<212> TYPE: PRT
<213> ORGANISM: Artificial sequence
<220> FEATURE:
<223> OTHER INFORMATION: Synthetic construct

<400> SEQUENCE: 2

Thr Pro Pro Ser Pro Phe
1               5

<210> SEQ ID NO 3
<211> LENGTH: 4
<212> TYPE: PRT
<213> ORGANISM: Artificial sequence
<220> FEATURE:
<223> OTHER INFORMATION: Synthetic construct
<220> FEATURE:
<221> NAME/KEY: misc_feature
<222> LOCATION: (2)..(3)
<223> OTHER INFORMATION: Xaa can be any naturally occurring amino acid

<400> SEQUENCE: 3

Pro Xaa Xaa Phe
1

<210> SEQ ID NO 4
<211> LENGTH: 4
<212> TYPE: PRT
<213> ORGANISM: Artificial sequence
<220> FEATURE:
<223> OTHER INFORMATION: Synthetic construct

<400> SEQUENCE: 4

Pro Ser Ser Pro
1

<210> SEQ ID NO 5
<211> LENGTH: 10
<212> TYPE: PRT
<213> ORGANISM: Artificial sequence
<220> FEATURE:
<223> OTHER INFORMATION: Synthetic construct

<400> SEQUENCE: 5

Leu Pro Ser Ser Pro Ser Ser Ser Ser Pro
1               5                   10

-continued

```
<210> SEQ ID NO 6
<211> LENGTH: 558
<212> TYPE: DNA
<213> ORGANISM: Rat

<400> SEQUENCE: 6
atgggggaac aacctatctt cagcactcga gctcatgtct tccagatcga cccaaacaca    60
aagaagaact gggtacccac cagcaagcat gcagttactg tgtcttattt ctatgacagc   120
acaaggaatg tgtataggat aatcagtcta gacggctcaa aggcaataat aaatagcacc   180
atcactccaa acatgacatt tactaaaaca tctcaaaagt ttggccaatg ggctgatagc   240
cgggcaaaca ctgtttatgg actgggattc tcctctgagc atcatctctc aaaatttgca   300
gaaaagtttc aggaatttaa agaagctgct cggctggcaa aggagaagtc gcaggagaag   360
atggaactga ccagtacccc ttcacaggaa tcagcaggag agatcttca gtctccttta    420 acaccagaaa gtatcaatgg acagatgat gagagaacac ccgatgtgac acagaactca    480
gagccaaggg ctgagccagc tcagaatgca ttgccatttt cacataggta cacattcaat   540
tcagcaatca tgattaaa                                                 558

<210> SEQ ID NO 7
<211> LENGTH: 186
<212> TYPE: PRT
<213> ORGANISM: Rat

<400> SEQUENCE: 7

Met Gly Glu Gln Pro Ile Phe Ser Thr Arg Ala His Val Phe Gln Ile
1               5                   10                  15

Asp Pro Asn Thr Lys Lys Asn Trp Val Pro Thr Ser Lys His Ala Val
                20                  25                  30

Thr Val Ser Tyr Phe Tyr Asp Ser Thr Arg Asn Val Tyr Arg Ile Ile
            35                  40                  45

Ser Leu Asp Gly Ser Lys Ala Ile Ile Asn Ser Thr Ile Thr Pro Asn
        50                  55                  60

Met Thr Phe Thr Lys Thr Ser Gln Lys Phe Gly Gln Trp Ala Asp Ser
65                  70                  75                  80

Arg Ala Asn Thr Val Tyr Gly Leu Gly Phe Ser Ser Glu His His Leu
                85                  90                  95

Ser Lys Phe Ala Glu Lys Phe Gln Glu Phe Lys Glu Ala Ala Arg Leu
            100                 105                 110

Ala Lys Glu Lys Ser Gln Glu Lys Met Glu Leu Thr Ser Thr Pro Ser
        115                 120                 125

Gln Glu Ser Ala Gly Gly Asp Leu Gln Ser Pro Leu Thr Pro Glu Ser
    130                 135                 140

Ile Asn Gly Thr Asp Asp Glu Arg Thr Pro Asp Val Thr Gln Asn Ser
145                 150                 155                 160

Glu Pro Arg Ala Glu Pro Ala Gln Asn Ala Leu Pro Phe Ser His Arg
                165                 170                 175

Tyr Thr Phe Asn Ser Ala Ile Met Ile Lys
            180                 185

<210> SEQ ID NO 8
<211> LENGTH: 5
<212> TYPE: RNA
<213> ORGANISM: Artificial sequence
<220> FEATURE:
<223> OTHER INFORMATION: Synthetic construct
```

```
<400> SEQUENCE: 8 auuua                                                              5

<210> SEQ ID NO 9
<211> LENGTH: 4
<212> TYPE: PRT
<213> ORGANISM: Artificial sequence
<220> FEATURE:
<223> OTHER INFORMATION: Synthetic construct

<400> SEQUENCE: 9

Ser Ser Thr Leu
1

<210> SEQ ID NO 10
<211> LENGTH: 4
<212> TYPE: PRT
<213> ORGANISM: Artificial sequence
<220> FEATURE:
<223> OTHER INFORMATION: Synthetic construct

<400> SEQUENCE: 10

Ser Ser Ser Leu
1

<210> SEQ ID NO 11
<211> LENGTH: 4
<212> TYPE: PRT
<213> ORGANISM: Rat

<400> SEQUENCE: 11

Ala Val Thr Val
1

<210> SEQ ID NO 12
<211> LENGTH: 4
<212> TYPE: PRT
<213> ORGANISM: Artificial sequence
<220> FEATURE:
<223> OTHER INFORMATION: Synthetic construct

<400> SEQUENCE: 12

Gly His Arg Phe
1

<210> SEQ ID NO 13
<211> LENGTH: 5
<212> TYPE: PRT
<213> ORGANISM: Artificial sequence
<220> FEATURE:
<223> OTHER INFORMATION: Synthetic construct

<400> SEQUENCE: 13

Leu Pro Pro Pro Phe
1               5

<210> SEQ ID NO 14
<211> LENGTH: 5
<212> TYPE: PRT
<213> ORGANISM: Artificial sequence
<220> FEATURE:
<223> OTHER INFORMATION: Synthetic construct

<400> SEQUENCE: 14

Leu Pro Pro Pro Arg
1               5
```

```
<210> SEQ ID NO 15
<211> LENGTH: 5
<212> TYPE: PRT
<213> ORGANISM: Artificial sequence
<220> FEATURE:
<223> OTHER INFORMATION: Synthetic construct

<400> SEQUENCE: 15

Leu Pro Leu Pro Phe
1               5

<210> SEQ ID NO 16
<211> LENGTH: 5
<212> TYPE: PRT
<213> ORGANISM: Artificial sequence
<220> FEATURE:
<223> OTHER INFORMATION: Synthetic construct

<400> SEQUENCE: 16

Leu Leu Pro Pro Phe
1               5

<210> SEQ ID NO 17
<211> LENGTH: 10
<212> TYPE: PRT
<213> ORGANISM: Artificial sequence
<220> FEATURE:
<223> OTHER INFORMATION: Synthetic construct

<400> SEQUENCE: 17

Leu Pro Ser Ser Ala Ser Ser Ser Ser Pro
1               5                   10

<210> SEQ ID NO 18
<211> LENGTH: 10
<212> TYPE: PRT
<213> ORGANISM: Artificial sequence
<220> FEATURE:
<223> OTHER INFORMATION: Synthetic construct

<400> SEQUENCE: 18

Ala Pro Ser Ser Pro Ser Ser Ser Ser Pro
1               5                   10

<210> SEQ ID NO 19
<211> LENGTH: 10
<212> TYPE: PRT
<213> ORGANISM: Artificial sequence
<220> FEATURE:
<223> OTHER INFORMATION: Synthetic construct

<400> SEQUENCE: 19

Leu Pro Ser Ser Pro Ser Ser Ser Ser Ala
1               5                   10

<210> SEQ ID NO 20
<211> LENGTH: 5
<212> TYPE: PRT
<213> ORGANISM: Artificial sequence
<220> FEATURE:
<223> OTHER INFORMATION: Synthetic construct

<400> SEQUENCE: 20

Leu Pro Ser Ser Pro
1               5
```

-continued

```
<210> SEQ ID NO 21
<211> LENGTH: 6
<212> TYPE: PRT
<213> ORGANISM: Artificial sequence
<220> FEATURE:
<223> OTHER INFORMATION: Synthetic construct
<220> FEATURE:
<221> NAME/KEY: misc_feature
<222> LOCATION: (3)..(4)
<223> OTHER INFORMATION: Xaa can be any naturally occurring amino acid

<400> SEQUENCE: 21

Pro Pro Xaa Xaa Phe Arg
1               5

<210> SEQ ID NO 22
<211> LENGTH: 4
<212> TYPE: PRT
<213> ORGANISM: Artificial sequence
<220> FEATURE:
<223> OTHER INFORMATION: Synthetic construct

<400> SEQUENCE: 22

Gly Leu Gly Phe
1

<210> SEQ ID NO 23
<211> LENGTH: 5
<212> TYPE: PRT
<213> ORGANISM: Artificial sequence
<220> FEATURE:
<223> OTHER INFORMATION: Synthetic construct
<220> FEATURE:
<221> NAME/KEY: misc_feature
<222> LOCATION: (3)..(3)
<223> OTHER INFORMATION: Xaa can be any naturally occurring amino acid

<400> SEQUENCE: 23

Leu Pro Xaa Pro Phe
1               5

<210> SEQ ID NO 24
<211> LENGTH: 10
<212> TYPE: PRT
<213> ORGANISM: Artificial sequence
<220> FEATURE:
<223> OTHER INFORMATION: Synthetic construct

<400> SEQUENCE: 24

Leu Ala Ser Ser Pro Ser Ser Ser Ser Pro
1               5                   10

<210> SEQ ID NO 25
<211> LENGTH: 810
<212> TYPE: PRT
<213> ORGANISM: Homo sapiens

<400> SEQUENCE: 25

Met Cys Pro Gly Ile Pro Gly Pro Arg Ala Glu Ala Ala Val Gly Thr
1               5                   10                  15

Thr His Pro Phe Ser Ser Pro Gly Ala Trp Leu Gly Ser Gly Ser Gly
                20                  25                  30

Ser Gly Pro Val Gly Ala Pro Pro Ser Pro Gly Leu Pro Pro Ser
        35                  40                  45

Trp Ala Ala Met Met Ala Ala Leu Tyr Pro Ser Thr Asp Leu Ser Gly
    50                  55                  60
```

-continued

```
Ala Ser Ser Ser Ser Leu Pro Ser Pro Ser Ser Ser Ser Pro Asn
 65                  70                  75                  80

Glu Val Met Ala Leu Lys Asp Val Arg Glu Val Lys Glu Glu Asn Thr
                 85                  90                  95

Leu Asn Glu Lys Leu Phe Leu Leu Ala Cys Asp Lys Gly Asp Tyr Tyr
            100                 105                 110

Met Val Lys Lys Ile Leu Glu Glu Asn Ser Ser Gly Asp Leu Asn Ile
            115                 120                 125

Asn Cys Val Asp Val Leu Gly Arg Asn Ala Val Thr Ile Thr Ile Glu
130                 135                 140

Asn Glu Asn Leu Asp Ile Leu Gln Leu Leu Asp Tyr Gly Cys Gln
145                 150                 155                 160

Lys Leu Met Glu Arg Ile Gln Asn Pro Glu Tyr Ser Thr Thr Met Asp
                165                 170                 175

Val Ala Pro Val Ile Leu Ala Ala His Arg Asn Asn Tyr Glu Ile Leu
            180                 185                 190

Thr Met Leu Leu Lys Gln Asp Val Ser Leu Pro Lys Pro His Ala Val
            195                 200                 205

Gly Cys Glu Cys Thr Leu Cys Ser Ala Lys Asn Lys Lys Asp Ser Leu
210                 215                 220

Arg His Ser Arg Phe Arg Leu Asp Ile Tyr Arg Cys Leu Ala Ser Pro
225                 230                 235                 240

Ala Leu Ile Met Leu Thr Glu Glu Asp Pro Ile Leu Arg Ala Phe Glu
                245                 250                 255

Leu Ser Ala Asp Leu Lys Glu Leu Ser Leu Val Glu Val Glu Phe Arg
            260                 265                 270

Asn Asp Tyr Glu Glu Leu Ala Arg Gln Cys Lys Met Phe Ala Lys Asp
            275                 280                 285

Leu Leu Ala Gln Ala Arg Asn Ser Arg Glu Leu Glu Val Ile Leu Asn
            290                 295                 300

His Thr Ser Ser Asp Glu Pro Leu Asp Lys Arg Gly Leu Leu Glu Glu
305                 310                 315                 320

Arg Met Asn Leu Ser Arg Leu Lys Leu Ala Ile Lys Tyr Asn Gln Lys
                325                 330                 335

Glu Phe Val Ser Gln Ser Asn Cys Gln Gln Phe Leu Asn Thr Val Trp
            340                 345                 350

Phe Gly Gln Met Ser Gly Tyr Arg Arg Lys Pro Thr Cys Lys Lys Ile
            355                 360                 365

Met Thr Val Leu Thr Val Gly Ile Phe Trp Pro Val Leu Ser Leu Cys
370                 375                 380

Tyr Leu Ile Ala Pro Lys Ser Gln Phe Gly Arg Ile Ile His Thr Pro
385                 390                 395                 400

Phe Met Lys Phe Ile Ile His Gly Ala Ser Tyr Phe Thr Phe Leu Leu
                405                 410                 415

Leu Leu Asn Leu Tyr Ser Leu Val Tyr Asn Glu Asp Lys Lys Asn Thr
            420                 425                 430

Met Gly Pro Ala Leu Glu Arg Ile Asp Tyr Leu Leu Ile Leu Trp Ile
            435                 440                 445

Ile Gly Met Ile Trp Ser Asp Ile Lys Arg Leu Trp Tyr Glu Gly Leu
            450                 455                 460

Glu Asp Phe Leu Glu Glu Ser Arg Asn Gln Leu Ser Phe Val Met Asn
465                 470                 475                 480
```

```
Ser Leu Tyr Leu Ala Thr Phe Ala Leu Lys Val Val Ala His Asn Lys
                485                 490                 495

Phe His Asp Phe Ala Asp Arg Lys Asp Trp Asp Ala Phe His Pro Thr
            500                 505                 510

Leu Val Ala Glu Gly Leu Phe Ala Phe Ala Asn Val Leu Ser Tyr Leu
            515                 520                 525

Arg Leu Phe Phe Met Tyr Thr Thr Ser Ser Ile Leu Gly Pro Leu Gln
        530                 535                 540

Ile Ser Met Gly Gln Met Leu Gln Asp Phe Gly Lys Phe Leu Gly Met
545                 550                 555                 560

Phe Leu Leu Val Leu Phe Ser Phe Thr Ile Gly Leu Thr Gln Leu Tyr
                565                 570                 575

Asp Lys Gly Tyr Thr Ser Lys Glu Gln Lys Asp Cys Val Gly Ile Phe
            580                 585                 590

Cys Glu Gln Gln Ser Asn Asp Thr Phe His Ser Phe Ile Gly Thr Cys
        595                 600                 605

Phe Ala Leu Phe Trp Tyr Ile Phe Ser Leu Ala His Val Ala Ile Phe
    610                 615                 620

Val Thr Arg Phe Ser Tyr Gly Glu Glu Leu Gln Ser Phe Val Gly Ala
625                 630                 635                 640

Val Ile Val Gly Thr Tyr Asn Val Val Val Ile Val Leu Thr Lys
                645                 650                 655

Leu Leu Val Ala Met Leu His Lys Ser Phe Gln Leu Ile Ala Asn His
            660                 665                 670

Glu Asp Lys Glu Trp Lys Phe Ala Arg Ala Lys Leu Trp Leu Ser Tyr
        675                 680                 685

Phe Asp Asp Lys Cys Thr Leu Pro Pro Phe Asn Ile Ile Pro Ser
    690                 695                 700

Pro Lys Thr Ile Cys Tyr Met Ile Ser Ser Leu Ser Lys Trp Ile Cys
705                 710                 715                 720

Ser His Thr Ser Lys Gly Lys Val Lys Arg Gln Asn Ser Leu Lys Glu
                725                 730                 735

Trp Arg Asn Leu Lys Gln Lys Arg Asp Glu Asn Tyr Gln Lys Val Met
            740                 745                 750

Cys Cys Leu Val His Arg Tyr Leu Thr Ser Met Arg Gln Lys Met Gln
        755                 760                 765

Ser Thr Asp Gln Ala Thr Val Glu Asn Leu Asn Glu Leu Arg Gln Asp
    770                 775                 780

Leu Ser Lys Phe Arg Asn Glu Ile Arg Asp Leu Leu Gly Phe Arg Thr
785                 790                 795                 800

Ser Lys Tyr Ala Met Phe Tyr Pro Arg Asn
                805                 810

<210> SEQ ID NO 26
<211> LENGTH: 742
<212> TYPE: PRT
<213> ORGANISM: Drosophila melanogaster

<400> SEQUENCE: 26

Asp Val Glu Lys Asn Phe Ile Leu Ser Cys Glu Arg Gly Asp Leu Pro
1               5                  10                  15

Gly Val Lys Lys Ile Leu Glu Glu Tyr Gln Gly Thr Asp Lys Phe Asn
            20                  25                  30

Ile Asn Cys Thr Asp Pro Met Asn Arg Ser Ala Leu Ile Ser Ala Ile
        35                  40                  45
```

-continued

```
Glu Asn Glu Asn Phe Asp Leu Met Val Ile Leu Leu Glu His Asn Ile
 50                  55                  60
Glu Val Gly Asp Ala Leu Leu His Ala Ile Ser Glu Glu Tyr Val Glu
 65                  70                  75                  80
Ala Val Glu Glu Leu Leu Gln Trp Glu Glu Thr Asn His Lys Glu Gly
                 85                  90                  95
Gln Pro Tyr Ser Trp Glu Ala Val Asp Arg Ser Lys Ser Thr Phe Thr
                100                 105                 110
Val Asp Ile Thr Pro Leu Ile Leu Ala Ala His Arg Asn Asn Tyr Glu
                115                 120                 125
Ile Leu Lys Ile Leu Leu Asp Arg Gly Ala Thr Leu Pro Met Pro His
130                 135                 140
Asp Val Lys Cys Gly Cys Asp Glu Cys Val Thr Ser Gln Thr Thr Asp
145                 150                 155                 160
Ser Leu Arg His Ser Gln Ser Arg Ile Asn Ala Tyr Arg Ala Leu Ser
                165                 170                 175
Ala Ser Ser Leu Ile Ala Leu Ser Ser Arg Asp Pro Val Leu Thr Val
                180                 185                 190
Phe Gln Leu Ser Trp Glu Leu Lys Arg Leu Gln Ala Met Glu Ser Glu
                195                 200                 205
Phe Arg Ala Glu Tyr Thr Glu Met Arg Gln Met Val Gln Asp Phe Gly
                210                 215                 220
Thr Ser Leu Leu Asp His Ala Arg Thr Ser Met Glu Leu Glu Val Met
225                 230                 235                 240
Leu Asn Phe Asn His Glu Pro Ser His Asp Ile Trp Cys Leu Gly Gln
                245                 250                 255
Arg Gln Thr Leu Glu Arg Leu Lys Leu Ala Ile Arg Tyr Lys Gln Lys
                260                 265                 270
Thr Phe Val Ala His Pro Asn Val Gln Gln Leu Leu Ala Ala Ile Trp
                275                 280                 285
Tyr Asp Gly Leu Pro Gly Phe Arg Arg Lys Gln Ala Ser Gln Gln Leu
                290                 295                 300
Met Asp Val Val Lys Leu Gly Cys Ser Phe Pro Ile Tyr Ser Leu Lys
305                 310                 315                 320
Tyr Ile Leu Ala Pro Asp Ser Glu Gly Ala Lys Phe Met Arg Lys Pro
                325                 330                 335
Phe Val Lys Phe Ile Thr His Ser Cys Ser Tyr Met Phe Phe Leu Met
                340                 345                 350
Leu Leu Gly Ala Ala Ser Leu Arg Val Val Gln Ile Thr Phe Glu Leu
                355                 360                 365
Leu Ala Phe Pro Trp Met Leu Thr Met Leu Glu Asp Trp Arg Lys His
                370                 375                 380
Glu Arg Gly Ser Leu Pro Gly Pro Ile Glu Leu Ala Ile Thr Tyr
385                 390                 395                 400
Ile Met Ala Leu Ile Phe Glu Glu Leu Lys Ser Leu Tyr Ser Asp Gly
                405                 410                 415
Leu Phe Glu Tyr Ile Met Asp Leu Trp Asn Ile Val Asp Tyr Ile Ser
                420                 425                 430
Asn Met Phe Tyr Val Thr Trp Ile Leu Cys Arg Ala Thr Ala Trp Val
                435                 440                 445
Ile Val His Arg Asp Leu Trp Phe Arg Gly Ile Asp Pro Tyr Phe Pro
450                 455                 460
```

```
Arg Glu His Trp His Pro Phe Asp Pro Met Leu Leu Ser Glu Gly Ala
465                 470                 475                 480

Phe Ala Ala Gly Met Val Phe Ser Tyr Leu Lys Leu Val His Ile Phe
            485                 490                 495

Ser Ile Asn Pro His Leu Gly Pro Leu Gln Val Ser Leu Gly Arg Met
        500                 505                 510

Ile Ile Asp Ile Ile Lys Phe Phe Ile Tyr Thr Leu Val Leu Phe
    515                 520                 525

Ala Phe Gly Cys Gly Leu Asn Gln Leu Leu Trp Tyr Tyr Ala Glu Leu
530                 535                 540

Glu Lys Asn Lys Cys Tyr His Leu His Pro Asp Val Ala Asp Phe Asp
545                 550                 555                 560

Asp Gln Glu Lys Ala Cys Thr Ile Trp Arg Arg Phe Ser Asn Leu Phe
                565                 570                 575

Glu Thr Ser Gln Ser Leu Phe Trp Ala Ser Phe Gly Leu Val Asp Leu
            580                 585                 590

Val Ser Phe Asp Leu Ala Gly Ile Lys Ser Phe Thr Arg Phe Trp Ala
        595                 600                 605

Leu Leu Met Phe Gly Ser Tyr Ser Val Ile Asn Ile Ile Val Leu Leu
    610                 615                 620

Asn Met Leu Ile Ala Met Met Ser Asn Ser Tyr Gln Ile Ile Ser Glu
625                 630                 635                 640

Arg Ala Asp Thr Glu Trp Lys Phe Ala Arg Ser Gln Leu Trp Met Ser
                645                 650                 655

Tyr Phe Glu Asp Gly Gly Thr Ile Pro Pro Phe Asn Leu Cys Pro
            660                 665                 670

Asn Met Lys Met Leu Arg Lys Thr Leu Gly Arg Lys Arg Pro Ser Arg
        675                 680                 685

Thr Lys Ser Phe Met Arg Lys Ser Met Glu Arg Ala Gln Thr Leu His
    690                 695                 700

Asp Lys Val Met Lys Leu Leu Val Arg Arg Tyr Ile Thr Ala Glu Gln
705                 710                 715                 720

Arg Arg Arg Asp Asp Tyr Gly Ile Thr Glu Asp Ile Ile Glu Val
                725                 730                 735

Arg Gln Asp Ile Ser Ser
            740
```

<210> SEQ ID NO 27
<211> LENGTH: 741
<212> TYPE: PRT
<213> ORGANISM: Drosophila melanogaster

<400> SEQUENCE: 27

```
Leu Glu Glu Lys Lys Phe Leu Leu Ala Val Glu Arg Gly Asp Met Pro
1               5                   10                  15

Asn Val Arg Arg Ile Leu Gln Lys Ala Leu Arg His Gln His Ile Asn
            20                  25                  30

Ile Asn Cys Met Asp Pro Leu Gly Arg Arg Ala Leu Thr Leu Ala Ile
        35                  40                  45

Asp Asn Glu Asn Leu Glu Met Val Glu Leu Leu Val Val Met Gly Val
50                  55                  60

Glu Thr Lys Asp Ala Leu Leu His Ala Ile Asn Ala Glu Phe Val Glu
65                  70                  75                  80

Ala Val Glu Leu Leu Leu Glu His Glu Glu Leu Ile Tyr Lys Glu Gly
            85                  90                  95
```

-continued

```
Glu Pro Tyr Ser Trp Gln Lys Val Asp Ile Asn Thr Ala Met Phe Ala
                100                 105                 110
Pro Asp Ile Thr Pro Leu Met Leu Ala Ala His Lys Asn Asn Phe Glu
            115                 120                 125
Ile Leu Arg Ile Leu Leu Asp Arg Gly Ala Ala Val Pro Val Pro His
        130                 135                 140
Asp Ile Arg Cys Gly Cys Glu Glu Cys Val Arg Leu Thr Ala Glu Asp
145                 150                 155                 160
Ser Leu Arg His Ser Leu Ser Arg Val Asn Ile Tyr Arg Ala Leu Cys
                165                 170                 175
Ser Pro Ser Leu Ile Cys Leu Thr Ser Asn Asp Pro Ser Ser Thr Ala
            180                 185                 190
Phe Gln Leu Ser Trp Glu Leu Arg Asn Leu Ala Leu Thr Glu Gln Glu
        195                 200                 205
Cys Lys Ser Glu Tyr Met Asp Leu Arg Arg Gln Cys Gln Lys Phe Ala
    210                 215                 220
Val Asp Leu Leu Asp Gln Thr Arg Thr Ser Asn Glu Leu Ala Ile Ile
225                 230                 235                 240
Leu Asn Tyr Asp Pro Gln Met Ser Ser Tyr Glu Pro Gly Asp Arg Met
                245                 250                 255
Ser Leu Thr Arg Leu Val Gln Ala Ile Ser Tyr Lys Gln Lys Lys Phe
            260                 265                 270
Val Ala His Ser Asn Ile Gln Gln Leu Leu Ser Ser Ile Trp Tyr Asp
        275                 280                 285
Gly Leu Pro Gly Phe Arg Arg Lys Ser Ile Val Asp Lys Val Ile Cys
    290                 295                 300
Ile Ala Gln Val Ala Val Leu Phe Pro Leu Tyr Cys Leu Ile Tyr Met
305                 310                 315                 320
Cys Ala Pro Asn Cys Arg Thr Gly Gln Leu Met Arg Lys Pro Phe Met
                325                 330                 335
Lys Phe Leu Ile His Ala Ser Ser Tyr Leu Phe Phe Leu Phe Ile Leu
            340                 345                 350
Ile Leu Val Ser Gln Arg Ala Asp Asp Phe Val Arg Ile Phe Gly
        355                 360                 365
Thr Thr Arg Met Lys Lys Glu Leu Ala Glu Gln Leu Arg Gln Arg
370                 375                 380
Gly Gln Thr Pro Ser Lys Leu Glu Leu Ile Val Val Met Tyr Val Ile
385                 390                 395                 400
Gly Phe Val Trp Glu Glu Val Lys Glu Ile Phe Ala Val Gly Met Lys
                405                 410                 415
Ser Tyr Leu Arg Asn Met Trp Asn Phe Ile Asp Phe Leu Arg Asn Ser
            420                 425                 430
Leu Tyr Val Ser Val Met Cys Leu Arg Ala Phe Ala Tyr Ile Gln Gln
        435                 440                 445
Ala Thr Glu Ile Ala Arg Asp Pro Gln Met Ala Tyr Ile Pro Arg Glu
    450                 455                 460
Lys Trp His Asp Phe Asp Pro Gln Leu Ile Ala Glu Gly Leu Phe Ala
465                 470                 475                 480
Ala Ala Asn Val Phe Ser Ala Leu Lys Leu Val His Leu Phe Ser Ile
                485                 490                 495
Asn Pro His Leu Gly Pro Leu Gln Ile Ser Leu Gly Arg Met Val Ile
            500                 505                 510
```

```
Asp Ile Val Lys Phe Phe Ile Tyr Thr Leu Val Leu Phe Ala Phe
            515                 520                 525

Ala Cys Gly Leu Asn Gln Leu Leu Trp Tyr Phe Ala Leu Glu Lys
        530                 535                 540

Ser Lys Cys Tyr Val Leu Pro Gly Gly Glu Ala Asp Trp Gly Ser His
545                 550                 555                 560

Gly Asp Ser Cys Met Lys Trp Arg Arg Phe Gly Asn Leu Phe Glu Ser
                565                 570                 575

Ser Gln Ser Leu Phe Trp Ala Ser Phe Gly Met Val Gly Leu Asp Asp
                580                 585                 590

Phe Glu Leu Ser Gly Ile Lys Ser Tyr Thr Arg Phe Trp Gly Leu Leu
            595                 600                 605

Met Phe Gly Ser Tyr Ser Val Ile Asn Val Ile Val Leu Leu Asn Leu
        610                 615                 620

Leu Ile Ala Met Met Ser Asn Ser Tyr Ala Met Ile Asp Glu His Ser
625                 630                 635                 640

Asp Thr Glu Trp Lys Phe Ala Arg Thr Lys Leu Trp Met Ser Tyr Phe
                645                 650                 655

Glu Asp Ser Ala Thr Leu Pro Pro Pro Phe Asn Val Leu Pro Ser Val
                660                 665                 670

Lys Trp Val Ile Arg Ile Phe Arg Lys Ser Ser Lys Thr Ile Asp Arg
            675                 680                 685

Gln Arg Ser Lys Lys Arg Lys Glu Gln Glu Gln Phe Ser Glu Tyr Asp
        690                 695                 700

Asn Ile Met Arg Ser Leu Val Trp Arg Tyr Val Ala Ala Met His Arg
705                 710                 715                 720

Lys Phe Glu Asn Asn Pro Val Ser Glu Asp Asp Ile Asn Glu Val Lys
                725                 730                 735

Ser Glu Ile Asn Thr
            740

<210> SEQ ID NO 28
<211> LENGTH: 754
<212> TYPE: PRT
<213> ORGANISM: Caenorhabditis elegans

<400> SEQUENCE: 28

Asn Asn Leu Phe Arg Phe Leu Glu Ala Ala Glu Leu Gly Asn Lys Pro
1               5                   10                  15

Thr Leu Gln Glu Cys Leu Asp Tyr Asp Gly Asp Arg Arg Leu Asn Val
            20                  25                  30

Asn Cys Leu Asp Ser Met Gly Arg Thr Ala Leu Glu Ile Ala Val Asp
        35                  40                  45

Asn Glu Asn Met Glu Val Val Glu Leu Leu Gln Gln Pro Asp Ile
    50                  55                  60

Arg Ile Gly Asn Ala Leu Leu Cys Ala Ile Arg Glu Gly Val Tyr Arg
65                  70                  75                  80

Leu Val Glu Val Leu Val Asn His Pro Asn Ile Thr Arg Glu Met Leu
                85                  90                  95

Gly Asp Gly Trp Ser Gln Ala Leu Asp Pro Ser Glu Ala Ala Ser Ala
            100                 105                 110

Glu Tyr Ser Ser Asp Ile Ser Pro Val Ile Leu Ala Ala Gln Leu Asn
        115                 120                 125

Gln Phe Glu Ile Leu Gln Met Leu Ile Arg Lys Asp Ala Ser Ile Glu
    130                 135                 140
```

-continued

```
Lys Pro His Arg His Ser Cys Ile Cys Glu Thr Cys Asp Arg Glu Arg
145                 150                 155                 160

Leu Asn Asp Ser Leu Gln Tyr Ser Leu Lys Arg Ile Asn Thr Phe Arg
            165                 170                 175

Ala Leu Ala Ser Pro Ala Trp Met Ser Leu Thr Ser Pro Asp Pro Ile
            180                 185                 190

Leu Ser Ala Phe Lys Leu Ser Trp Asp Leu Gln Arg Leu Ala Phe Glu
            195                 200                 205

Glu His Glu Phe Lys Glu Thr Tyr Leu Gln Leu Ser Glu Gln Cys Lys
            210                 215                 220

Gln Tyr Ser Cys Asp Leu Leu Ser Gln Cys Arg Ser Ser Glu Glu Val
225                 230                 235                 240

Ile Ala Ile Leu Asn Lys Asp Gly Asn Val Asn Asp Asp Asn Ile Asp
            245                 250                 255

Val Trp Ala Ser Lys Leu Ser Leu Ser Arg Leu Lys Leu Ala Ile Lys
            260                 265                 270

Tyr Glu Gln Lys Ala Phe Val Ser His Pro His Cys Gln Gln Leu Leu
            275                 280                 285

Thr Ser Ile Trp Tyr Glu Gly Ile Pro Tyr Arg Gln Arg Ser Gly Thr
290                 295                 300

Trp Ala Asn Phe Phe Leu Tyr Ala Phe Leu Leu Phe Leu Trp Pro Ile
305                 310                 315                 320

Phe Cys Leu Met Tyr Ile Leu Met Pro Lys Ser Arg Leu Gly Arg Leu
            325                 330                 335

Val Arg Ser Pro Phe Met Lys Phe Phe Tyr Tyr Ser Val Ser Phe Ala
            340                 345                 350

Thr Phe Leu Gly Leu Leu Thr Trp Ala Thr Phe Glu Asp Tyr Arg Tyr
            355                 360                 365

Glu Lys Gly Glu Arg Gly Gly Met Thr Arg Ala Ser Asp Arg Gly Pro
            370                 375                 380

Pro Ala Thr Trp Val Glu Ser Leu Val Phe Thr Trp Val Ile Gly Met
385                 390                 395                 400

Leu Trp Ser Glu Ile Lys Gln Leu Trp Glu Glu Gly Phe Lys Arg Tyr
            405                 410                 415

Met Arg Gln Trp Trp Asn Trp Leu Asp Phe Leu Met Ile Cys Leu Tyr
            420                 425                 430

Leu Cys Thr Ile Ser Ile Arg Leu Ser Ala Tyr Tyr Ile Phe Thr Tyr
            435                 440                 445

Arg Glu Asp Pro Tyr Arg Tyr Thr Val Arg Thr Tyr Trp Thr Ser Glu
450                 455                 460

Glu Pro Met Leu Val Ala Glu Ala Leu Phe Ala Val Gly Asn Val Phe
465                 470                 475                 480

Ser Phe Ala Arg Ile Ile Tyr Leu Phe Gln Thr Asn Pro Tyr Leu Gly
            485                 490                 495

Pro Leu Gln Ile Ser Leu Gly Cys Met Leu Val Asp Val Ala Lys Phe
            500                 505                 510

Cys Phe Ile Phe Val Leu Ile Ile Ser Ser Phe Ser Ile Gly Leu Ala
            515                 520                 525

Gln Leu Tyr Trp Tyr Tyr Asp Pro Asn Thr Asp Val Cys Leu Pro Gly
            530                 535                 540

Ala Thr Cys Lys His Ser Ser Asn Val Phe Ser Ser Ile Ala Asp Ser
545                 550                 555                 560
```

```
Tyr Leu Thr Leu Leu Trp Ser Leu Phe Ser Ile Thr Lys Pro Glu Asp
                565                 570                 575

Thr Asp Val Val Glu Asn His Lys Ile Thr Gln Trp Val Gly Gln Gly
            580                 585                 590

Met Phe Ile Met Tyr His Cys Thr Ser Ile Ile Val Leu Leu Asn Met
        595                 600                 605

Leu Ile Ala Met Met Ser His Ser Phe Gln Ile Asn Asp His Ala
    610                 615                 620

Asp Leu Glu Trp Lys Phe His Arg Thr Lys Leu Trp Met Ala His Phe
625                 630                 635                 640

Asp Glu Gly Ser Ser Leu Pro Pro Phe Asn Ile Ile Val Thr Pro
                645                 650                 655

Lys Ser Leu Ile Tyr Val Met Asn Cys Leu Phe Asn Thr Val Arg Trp
                660                 665                 670

Leu Leu Gly Lys Tyr Thr Tyr Gln Lys Asn Arg Asn Arg Ala Thr Ile
                675                 680                 685

Arg Arg Pro Gly Tyr Ser Arg Lys Arg Asn Glu Met Glu Lys Ser Gly
            690                 695                 700

Gly His Asp Asp Asp Ser Leu Lys Pro Leu Thr Tyr Ala Asp Ile Ile
705                 710                 715                 720

Thr Arg Leu Val Ala Arg Phe Ile His Gln Thr Lys Lys Asp Met Lys
                725                 730                 735

Met Asp Gly Val Asn Glu Asp Asp Leu His Glu Ile Lys Gln Asp Ile
                740                 745                 750

Ser Ser

<210> SEQ ID NO 29
<211> LENGTH: 183
<212> TYPE: PRT
<213> ORGANISM: Homo sapiens

<400> SEQUENCE: 29

Gln Phe Leu Phe Trp Thr Met Phe Gly Met Glu Glu His Ala Val Val
1               5                   10                  15

Asp Val Pro Gln Phe Leu Val Pro Glu Phe Ala Gly Arg Ala Leu Tyr
            20                  25                  30

Gly Ile Phe Thr Ile Ile Met Val Ile Val Leu Leu Asn Met Leu Ile
        35                  40                  45

Ala Met Ile Thr Asn Ser Phe Gln Lys Ile Glu Asp Asp Ala Asp Val
    50                  55                  60

Glu Trp Thr Phe Ala Arg Ser Lys Leu Tyr Leu Phe Tyr Phe Glu Gly
65                  70                  75                  80

Leu Thr Leu Pro Val Pro Phe Asn Ile Leu Pro Ser Ser Lys Ala Val
                85                  90                  95

Phe Tyr Leu Leu Arg Arg Ile Cys Gln Phe Ile Cys Cys Cys Cys Ser
                100                 105                 110

Cys Cys Lys Thr Lys Lys Pro Asp Tyr Pro Ile Ile Thr Phe Ala
            115                 120                 125

Asn Pro Arg Ala Gly Ala Val Pro Gly Glu Gly Glu Arg Gly Ser Tyr
        130                 135                 140

Arg Leu His Val Ile Lys Ala Leu Val Gln Arg Tyr Thr Glu Thr Ala
145                 150                 155                 160
```

-continued

```
Arg Arg Glu Phe Glu Glu Thr Arg Arg Lys Asp Leu Gly Asn Arg Leu
                165                 170                 175

Thr Glu Leu Thr Lys Thr Ile
            180

<210> SEQ ID NO 30
<211> LENGTH: 117
<212> TYPE: PRT
<213> ORGANISM: Homo sapiens

<400> SEQUENCE: 30

Thr Ser Val Val Leu Lys Tyr Asp His Lys Phe Ile Glu Asn Ile Gly
1               5                   10                  15

Tyr Val Leu Tyr Gly Ile Tyr Asn Val Thr Met Val Val Val Leu Leu
            20                  25                  30

Asn Met Leu Ile Ala Met Ile Asn Ser Ser Tyr Gln Glu Ile Glu Asp
            35                  40                  45

Asp Ser Asp Val Glu Trp Lys Phe Ala Arg Ser Lys Leu Trp Leu Ser
50                  55                  60

Tyr Phe Asp Asp Gly Lys Thr Leu Pro Pro Pro Phe Ser Leu Val Pro
65                  70                  75                  80

Ser Pro Lys Ser Phe Val Tyr Phe Ile Met Arg Ile Val Asn Phe Pro
                85                  90                  95

Lys Cys Arg Arg Arg Arg Leu Gln Lys Asp Ile Gly Asn Gly Glu Trp
                100                 105                 110

Gly Asn Ser Lys Ser
            115
```

METHOD OF SCREENING FOR AGENTS THAT MODULATE A HOMER SIGNALING PATHWAY

BACKGROUND OF THE INVENTION

1. Field of the Invention

The invention relates generally to signal transduction in the modulation of immunosuppression and neuroprotection and, more specifically, to the exploitation of the mechanism of immunophilin/peptidylproline cis-trans isomerase (PPIase) and Homer interaction in the development of therapeutic reagents.

2. Background Information

Many natural products are high affinity ligands to cellular proteins involved in signal transduction which are key to regulating cell growth, division and differentiation. One family of such natural products are the immunosuppressive drugs cyclosporin A (CsA), FK506 and rapamycin (Luan S., Bot Bull Acad Sin (1998) 39:217-223).

Cellular studies suggest that all three drugs suppress the immune response by blocking the activation of T lymphocytes (Schreiber S., Science (1991) 251:283-287; Kunz and Hall, Biochem Sci (1993) 18:334-338). CsA and FK506 inhibit a $Ca^{2+}$-dependent signaling pathway involved in activation of T cell receptors, while rapamycin blocks a $Ca^{2+}$-independent pathway required for the proliferation of T cells upon stimulation by lymphokines such as interleukin-2 (Schreiber and Crabtree, Immunol Today (1992) 13:136-141; Sigal and Dumont, Ann Rev Immunol (1992) 10:519-560). In addition to blocking T cell activation, these drugs also have inhibitory effects on signaling pathways in other systems. For example, CsA and FK506 both block the $Ca^{2+}$-dependent degranulation in mast cells (Hultsch et al., 1991). Rapamycin, on the other hand, has been shown to arrest yeast and some mammalian cells at the G1 phase in the cell cycle (Heitman et al., Science (1991) 253:905-909; Bierer et al., Proc Natl Acad Sci USA (1990) 250:556-559; Dumont et al., J Immunol (1990) 144:1418-1424; Price et al., Science (1992) 257:973-977). These findings suggest that CsA, FK506 and rapamycin may target molecules that are common signaling components in different systems.

To understand the molecular mechanisms of immunosuppression by CsA, FK506, and rapamycin, the cellular receptors of these drugs have been purified and characterized (reviewed by Schreiber, 1991; Fruman et al., FASEB J (1994) 8:391-400). CsA binds to a family of receptors named cyclophilins (CyPs), and FK506 and rapamycin bind to a distinct set of receptors called FKBPs (i.e., FK506 and rapamycin-Binding Proteins). These receptors are collectively referred to as immunophilins (Schreiber, 1991).

Immunophilins have been shown to have peptidylproline cis-trans isomerase (PPIase or rotamase) activity (Harding et al., Nature (1989) 341:758-760; Fischer et al., Nature (1989) 337:476-478). Subsequent investigations have shown that the enzyme activity of both CyPs and FKBPs are competitively inhibited by binding of their specific ligands (Kofron et al., Biochemistry (1991) 30:6127-6134; Fesik et al., Science (1990) 250:1406-1409; Van Duyne et al., Science (1991) 252:839-842). However, some drug analogs can inhibit rotamase activity yet fail to suppress the immune response (Bierer et al., 1990). In particular, FK506 and rapamycin bind to exactly the same set of receptors but have different modes of action (Dumont et al., 1990; Bierer et al., 1990).

Nevertheless, it appears that the complexes formed by immunophilin and their ligands are the functional module for immunosuppression (see, e.g., Liu et al., Cell (1991) 66:807-815). For example, it has been demonstrated that the FKBP12-FK506 and CyP-CsA complexes, but not their separate components, bind to and inhibit the activity of calcineurin. Biochemical and cellular transfection studies have demonstrated that inhibition of calcineurin activity is necessary for the immunosuppressive effect of CsA and FK506 (Liu et al., Biochemistry (1992) 31:3896-3901; O'Keefe et al., Nature (1992) 357:692-694; Clipstone and Crabtree, Nature (1992) 357:695-697). In contrast, the complex formed by FKBP12 and rapamycin targets a 220 kDa protein referred to as FRAP (FKBP-Rapamycin Associated Protein) or RAFT1 (Rapamycin And FKBP12 Targets), a mammalian homologue of TOR1 and TOR2 in yeast that are involved in the signaling pathway leading to G1-S progression in the cell cycle (Kunz et al., Trends Biochem Sci (1993) 18:334-338; Brown et al., Nature (1994) 369:756-758; Sabatini et al., Cell (1994) 78:35-43).

PPIase inhibitors are used clinically as immunosuppressants, but also have neuroprotective actions (Guo et al., 2001; Snyder et al., 1998). As stated above, their immunosuppressive activity is thought to arise from secondary inhibition of the phosphatase calcineurin, however, their mechanism of neuroprotective activity remains obscure. For example, while immunophilins inhibitors have been characterized that bind to the FKBP family of proteins and inhibit rotamase activity (supra), there is no clear relationship between this activity and therapeutic efficacy. In fact, their therapeutic efficacy remains controversial and clinical trials for treatment of diseases, such as Parkinson's Disease, recently failed (Gold and Nutt, 2002). It is therefore important to understand the molecular basis for activity of PPIase agents so that simple assays can be established to screen for optimally effective compounds.

The present disclosure describes a novel mechanism of action of PPIases. Several lines of evidence indicate that the PPIase family of proteins regulate the binding of a protein described as "Homer" (see, e.g., U.S. Pat. No. 6,294,355, herein incorporated by reference, for a description of this protein) to its targets. This regulation is mediated in part by competition in binding to the Homer interacting proteins.

Homer was originally identified based on its rapid transcriptional induction in brain neurons in response to depolarizing stimuli (Brakeman et al., 1997). Homer mRNA induction does not require new protein synthesis, indicating that it is an immediate early gene (IEG). The IEG form of Homer was the founding member of a family of three mammalian genes termed Homer 1, 2 and 3 (Xiao et al., 1998; Xiao et al., 2000). The human genome also includes a Homer 2-like pseudogene.

All Homer transcripts encode an N-terminal EVH1 domain which is named based on homology to *Drosophila* Ena and mammalian Vasp (Xiao et al., 2000). The EVH1 domains of the three mammalian Homer genes are conserved at ~90% identity. In the initial report that described Homer IEG (now termed Homer 1a), it was also demonstrated that Homer 1a binds the C-terminus of group 1 metabotropic glutamate receptors (Brakeman et al., 1997). In subsequent work, the site of interaction in the metabotropic receptor and a consensus sequence for binding of Homer (Tu et al., 1998) have been identified. The core consensus sequence is PPXXF (SEQ ID NO:1), termed the Homer ligand (now termed type 1 Homer ligand). The EVH1 domain interaction with the Homer ligand was further defined by a co-crystal of Homer 1 and a synthetic peptide (Beneken et al., 2000).

The co-crystal determined that the EVH1 fold is isomorphic to the plextrin homology (PH) domain (FIG. 1). The co-crystal also identified surfaces of interaction with the Homer ligand and rationalized the consensus sequence of the Homer ligand. Critical sites of contact include an association between the second proline (TPPSPF, SEQ ID NO: 2) and tryptophan W24 in the Homer 1 EVH1, and between the phenylalanine and a pocket that extends to glycine 89 of the EVH1 domain (Beneken et al., 2000). The critical contribution of these sites of interaction to the overall energetics of binding was confirmed in assays of binding that used point mutants of the EVH1 domain. The crystal also indicated that the original consensus sequence PPXXFR SEQ ID NO:21) should be modified to PXXF (SEQ ID NO:3) since the first proline is not essential for contact with the EVH1 domain. The first proline may contribute to the overall conformation of the local protein sequence. The contact at the second proline involves the amino acid backbone and not the proline side chain, so other amino acids could, in principle, substitute for proline. Additional prolines are common in natural Homer ligands and are rationalized to be important in defining the correct configuration of the ligand for binding, but not in direct contact with the EVH1 binding surface. Perhaps most importantly, the co-crystal demonstrated that the binding surface of the proline is similar to that of related EVH1 domains of Ena, Mena and Vasp, but the surface for the phenylalanine is unique to the Homer subfamily. Thus, it has been concluded that the Homer genes are a subfamily of the EVH1 family which possess unique binding surfaces and ligand sequence recognition.

All verified Homer transcripts, with the exception of Homer 1a, also encode a C-terminal coiled-coil motif (Xiao et al., 1998; Xiao et al., 2000). The coiled-coil domain mediates self-oligomerization. By forming self multimers, Homer proteins can bind to target proteins and induce them to remain in close physical association. In addition to the group 1 metabotropic glutamate receptors, Homer proteins bind to inositol trisphosphate receptor (IP3R) (Tu et al., 1998), the ryanodine receptor (RyR) (Feng et al., 2002), the scaffolding protein family termed Shank (Tu et al., 1999), and several novel gene transcripts (see, e.g., U.S. Pat. No. 6,294,355 and U.S. Application No. 2003/0027147, each herein incorporated by reference in their entirety).

Homer 1a is distinct from other Homer gene transcripts in that it is expressed as an immediate early gene and does not encode a coiled-coil domain, thus, it cannot self multimerize (Xiao et al., 1998). Based on these differences in expression dynamics and protein function, it is hypothesized that Homer 1a functions as a natural dominant negative protein to regulate the degree of coupling of Homer binding partners (Xiao et al., 2000). In physiological studies, it has been demonstrated that Homer 1a reduces coupling of mGluR to intracellular IP3R (Tu et al., 1998) and increases coupling of mGluR5 to membrane ion channels (Kammermeier et al., 2000).

One of the central uncertainties in Homer function concerns the regulation of binding. The co-crystal of Homer EVH1 and mGluR5 peptide provided an important clue in that the ligand (TPPSPF, SEQ ID NO:2) assumed a specific structural conformation. Importantly, the prolines are required to be in specific configurations that are in trans for the first two prolines and in cis for the SPF. The trans configuration is energetically preferred in most sequences, so this raises the possibility that interaction between Homer and mGluR5 (or other binding partners) may be regulated by the conformational state of the proline sequence.

All known Homer ligands include prolines, which are conformationally restricted and require the activity of cis-trans prolyl isomerases to interconvert (FIG. 2). Accordingly, the possibility was considered that PPIases play a role in regulating Homer binding to its ligands. The present invention describes a mechanism of action for signal transduction which includes Homer and PPIase interaction.

Several lines of evidence indicate that the PPIase family of proteins regulate the binding of Homer to its targets. This regulation is mediated in part by competition in binding to the Homer interacting proteins. Two protein targets that have been presently identified, which are bound by both Homer and PPIases, include mGluR5 and TrpC1. Further, it has been determined that Homer and representative PPIases bind to the same target sequence in mGluR5/TrpC1 and that there are competitive interactions that regulate their respective binding.

Immunophilins bind to PPIases and disrupt their interaction with mGluR5/TrpC1. A consequence of this disruption is that Homer can more effectively bind to mGluR5 and TrpC1. Moreover, it appears that Homer and PPIases functions are naturally interdependent; PPIases may compete for Homer binding and thereby block the formation of signaling complexes. It also appears that PPIase activity is required to place the mGluR5 sequence in the correct confirmation for Homer to bind. These findings have important implications for the development of novel PPIase agents that selectively modulate Homer signaling pathways.

Using this mechanism of action, the present invention permits implementation of simple, robust and reliable high throughput assays that can identify a novel pharmacology of PPIase inhibitors that modulate Homer signaling.

SUMMARY OF THE INVENTION

The present invention provides a rationale and means for development of new classes of compounds that have broader effective dose ranges and optimal therapeutic efficacy than the present immunophilin/PPIase inhibitors. Assays are disclosed that identify agents which modify the binding of Homer to specific target proteins. Target proteins are selected based on either known interaction with Homer or presence of either a proline type 1 or proline type 2 Homer ligand consensus sequence. For example, Homer interacting proteins include, but are not limited to, mGluR1a, mGluR5 (Brakeman et al., 1997), Shank family members (Tu et al., 1999), IP3 receptor (Tu et al., 1998), ryanodine receptor (Feng et al., 2002), TrpC1 and the set of Homer interacting proteins related to synapse activation (See, e.g., U.S. Pat. No. 6,294,355 and U.S. Pat. App. No. 20030027147). Further such proteins include, but are not limited to, other members of the Trp family and the related family including the vanilloid receptors (Montell et al., 2002).

Further, the present invention demonstrates that PPIase inhibitor effects are biphasic and dependent on both the dose and time of exposure. Thus, because known PPIase inhibitors modulate Homer binding at doses that are identical to those known to be effective in vivo, novel agents can be selectively identified by exploiting PPIase/Homer interaction and the biphasic nature of the PPIase/inhibitor response occurring over a dose range that is typically considered to be within the therapeutic range.

In addition, a novel Homer binding site, termed a type 2 Homer ligand that is also sensitive to PPIase modulation, is disclosed which defines a new family of Homer target proteins.

In one embodiment, disclosed assays are useful in screening for agents which modulate a Homer signaling pathway and include contacting polypeptides, proteins and/or fragments thereof having a proline-type Homer ligand consensus sequence with test agents. Subsequent steps may include contacting the consensus sequence containing polypeptide or protein with a Homer protein to determine whether binding between the Homer and the polypeptide and Homer protein is increased or decreased, where increased or decreased binding between the consensus containing polypeptide and Homer protein is indicative of the presence of a modulating agent for a Homer signaling pathway. In one aspect, the determining step includes immunoprecipitation of a complex formed between the consensus containing protein/polypeptide and the Homer protein.

In another aspect, the method is useful in screening for agents that have neuroprotective properties that may serve as effective therapeutic modalities against illnesses including, but not limited to, peripheral neuropathies and neurological pathologies related to neurodegeneration.

In another aspect, agents are added to cells or cell lysates and the effect of the agent is assessed based on the ability of Homer to bind a specific protein. In one aspect, assays are described which can be used to screen for agents that modify TrpC1 or mGluR5 binding to GST-Homer.

In one aspect, the method is useful in screening for agents that have immunosuppressive properties that may be effective as therapeutic modalities against illnesses including, but not limited to, psoriasis, inflammatory bowel disease (such as Crohn's disease and ulcerative colitis), adult respiratory distress syndrome, dermatitis, meningitis, encephalitis, eczema, asthma and other conditions involving infiltration of T cells and chronic inflammatory responses, skin hypersensitivity reactions, atherosclerosis, leukocyte adhesion deficiency, rheumatoid arthritis, systemic lupus erythematosus (SLE), diabetes mellitus, multiple sclerosis, Reynaud's syndrome, autoimmune thyroiditis, experimental autoimmune encephalomyelitis, Sjorgen's syndrome, juvenile onset diabetes, and immune responses associated with delayed hypersensitivity mediated by cytokines and T-lymphocytes typically found in tuberculosis, sarcoidosis, polymyositis, granulomatosis and vasculitis, pernicious anemia, diseases involving leukocyte diapedesis, CNS inflammatory disorder, multiple organ injury syndrome secondary to septicemia or trauma, autoimmune hemolytic anemia, myasthenia gravis; antigen-antibody complex mediated diseases and transplantations, including graft vs. host or host vs. graft disease.

In a related aspect, the consensus containing polypeptide/protein and Homer protein are included in a cell or cell lysate. Further, the Homer ligand consensus sequence may be a proline-type 1 Homer ligand consensus sequence or a proline-type 2 Homer ligand consensus sequence, where the consensus sequence is denoted as set forth in SEQ ID Nos: 1 and 4, respectively.

In another aspect, the assay includes an amino acid sequence having a homer ligand consensus sequence, where the sequence can be selected from proteins including, but not limited to, synphilin, EF2kinase, p70, Notch 4, AGIE-BP1, cytosolic thymidine kinase, neuronal PAS domain protein 2, zona pellucida sperm binding protein 3 precursor, Shank family of proteins, ryanodine receptor (RYR or sarcoplasmic reticulum calcium release channel), p82, androgen receptor, TrpC1, mGluR1a and mGluR5.

In one aspect, the assay may further include contacting the consensus containing amino acid sequence with a PPIase inhibitor in the presence of a PPIase. In a related aspect, a PPIase inhibitor includes, but is not limited to, a rotamase inhibitor. In another aspect, the PPIase inhibitor may include FK506, cyclosporin A, or GPI1046.

In one aspect, the method includes, but is not limited to, PPIases of the FKBP family, cyclophilin family, and Pin family of PPIases, for example. In a related aspect, the PPIase is FKBP12 or FKBP52.

In one aspect, the method includes a human Homer protein. However, the Homer protein may include, but is not limited to, the amino acid sequences as set forth in the accession number as provided herein.

In one embodiment, a method of screening is disclosed for identifying Homer modulating agents which includes contacting transformed cells expressing recombinant amino acid sequences having a proline-type Homer ligand consensus sequence with a PPIase inhibitor and Homer protein in the presence or absence of a test agent to determine whether the agent decreases binding of Homer protein to the amino acid sequence, where decreased binding of the Homer protein to the amino acid sequence as agent concentration is increased indicates the presence of a competitive Homer ligand. In one aspect, the method includes, but is not limited to, PPIases of the FKBP family, cyclophilin family, and Pin family of PPIases, for example. In a related aspect, the PPIase is FKBP12 or FKBP52.

In one aspect, the modulating agent functions as a neuroprotective or immuno-suppressive agent.

In another aspect, binding may be determined by an end-point assay that includes, but is not limited to, modulation of $Ca^{+2}$ signaling, modulation of phospholipase C (PLC), modulation of Trp channels, modulation of MAP linase, modulation of phosphoinositide-3-kinase (PI3kinase), modulation of ion channels, modulation of inositol 1,4,5-trisphosphate receptor/$Ca^{+2}$ (IP3) channels, modulation of RYR channels, and modulation of growth factor dependent responses.

In one aspect, the method includes a human Homer protein. However, the Homer protein may include, but is not limited to, the amino acid sequences as set forth in the accession numbers provided herein.

In one embodiment, a method of screening is disclosed for compounds which selectively modulate Homer binding in the presence of at least one PPIase inhibitor, where the PPIase inhibitor shows a biphasic affect at separate concentrations. In one aspect, the method includes contacting a transformed cell expressing a PPIase and a Homer ligand consensus containing amino acid sequence with a PPIase inhibitor at a concentration that does not inhibit Homer binding to the amino acid sequence and a separate transformed cell at a concentration that does inhibit Homer protein binding to the amino acid sequence. In another related aspect, the transformed cells are subsequently contacted with a test agent, and the Homer protein and the ligand consensus containing amino acid sequence interaction is determined, where modulation of the interaction by the agent at the concentration of PPIase inhibitor which does not inhibit binding of the Homer protein is indicative of the presence of a compound which selectively modulates Homer binding. In one aspect, the PPIase inhibitor is GPI 1046.

In another aspect, the assay includes an amino acid sequence having a homer ligand consensus sequence, where the sequence can be selected from proteins including, but not limited to, synphilin, EF2kinase, p70, Notch 4, AGIE-BP1, cytosolic thymidine kinase, neuronal PAS domain protein 2, zona pellucida sperm binding protein 3 precursor, Shank family of proteins, ryanodine receptor, p82, androgen receptor, TrpC1, mGluR1a and mGluR5.

In one aspect, binding maybe determined by an endpoint assay that includes, but is not limited to, modulation of $Ca^{+2}$ signaling, modulation of PLC, modulation of Trp channels, modulation of MAP kinase, modulation of PI3kinase, modulation of ion channels, modulation of IP3 channels, modulation of RYR channels, and modulation of growth factor dependent responses.

In one embodiment, synthetic oligopeptides are disclosed, including oligopeptides having at least 4 amino acid residues, but not more than 10 amino acid residues. In one aspect, the synthetic oligopeptides has a consensus sequence as set forth in SEQ ID NO: 4.

In another embodiment, a synthetic oligopeptide as set forth as SEQ ID NO: 5 is disclosed.

In one aspect, nucleic acids encoding synthetic oligopeptides are disclosed, including nucleic acids encoding oligopeptides having at least 4 amino acid residues, but not more than 10 amino acid residues, having a consensus sequence as set forth in SEQ ID NO: 4. In another aspect, nucleic acids are envisaged encoding the oligopeptide as set forth in SEQ ID NO: 4.

In one embodiment, a nucleic acid as set forth in SEQ ID NO:6 is disclosed.

In one embodiment, a method of preserving nerve bundles after surgery by administering to a subject in need thereof a therapeutic amount of a pharmaceutical composition which includes an agent identified by the methods disclosed in the present invention is described.

In one aspect, the agent is administered during or subsequent to a surgical procedure. In another aspect, the surgical procedure involves neurological ailments. In a further aspect, the surgical procedure includes, but is not limited to, radical prostatectomy, organ transplantation, trauma, and stroke.

In another embodiment, a method of modulating sensory perception by administering to a subject in need thereof a therapeutic amount of a pharmaceutical composition which includes an agent identified by the methods disclosed in the present invention is described. In a related aspect, the sensory perception is tactile or temperature perception.

In another embodiment, a method of treating a neurological disorder by administering to a subject in need thereof a therapeutic amount of a pharmaceutical composition which includes an agent identified by the methods disclosed in the present invention is described. In one aspect, the neurological disorder includes, but is not limited to, peripheral neuropathies and neurological pathologies related to neurodegeneration. In another aspect, the disorder includes, but is not limited to, Alzheimer's disease, Parkinson's disease and amyotrophic lateral sclerosis.

In one embodiment, a method of inducing immunosuppression or treating inflammation by administering to a subject in need thereof a therapeutic amount of a pharmaceutical composition which includes an agent identified by the methods disclosed in the present invention is described.

In a related aspect, inducing immunosuppression is effective for treating disorders including psoriasis, inflammatory bowel disease (such as Crohn's disease and ulcerative colitis), adult respiratory distress syndrome, dermatitis, meningitis, encephalitis, eczema, asthma and other conditions involving infiltration of T cells and chronic inflammatory responses, skin hypersensitivity reactions, atherosclerosis, leukocyte adhesion deficiency, rheumatoid arthritis, systemic lupus erythematosus (SLE), diabetes mellitus, multiple sclerosis, Reynaud's syndrome, autoimmune thyroiditis, experimental autoimmune encephalomyelitis, Sjorgen's syndrome, juvenile onset diabetes, and immune responses associated with delayed hypersensitivity mediated by cytokines and T-lymphocytes typically found in tuberculosis, sarcoidosis, polymyositis, granulomatosis and vasculitis, pernicious anemia, diseases involving leukocyte diapedesis, CNS inflammatory disorder, multiple organ injury syndrome secondary to septicemia or trauma, autoimmune hemolytic anemia, myasthenia gravis, antigen-antibody complex mediated diseases, and transplantations, including graft vs. host or host vs. graft disease.

In one embodiment, a method of treating hematological disorders by administering to a subject in need thereof a therapeutic amount of a pharmaceutical composition which includes an agent identified by the methods disclosed in the present invention is described. In one aspect, the hematological disorders include, but is not limited to, lymphoblastic leukemia, acute or chronic myelogenous leukemia, Hodgkin's lymphoma, Non-Hodgkin's lymphoma, myelodysplastic syndrome, multiple myeloma, and chronic lymphocytic leukemia.

In one embodiment, methods of diagnosing a homer signaling disorder are disclosed and include isolating and lysing biological samples from subjects suspected of exhibiting symptoms due to a pathological condition attributable to such a disorder. Subsequent steps may include lysing such samples in the presence of a PPIase inhibitor and contacting the lysed samples with one or more proteins or peptides that have a proline-type Homer ligand consensus sequence and a Homer protein, to determining whether protein or peptide and Homer protein bind. In one aspect, decreased binding between the consensus containing protein or peptide and the Homer protein is indicative of a Homer signaling disorder.

In another aspect, a method is disclosed where the disorder is associated with increased PPIase activity. Such disorders may include but are not limited to immunosuppressive disorders, hematological disorders or neurological disorders.

In one embodiment, a method is described for determining the efficacy of a PPIase inhibitor including determining such efficacy when the inhibitor demonstrates a biphasic effect on Homer binding to one or more proteins or peptides, where the increased or decreased binding between a Homer protein and the one or more proteins or peptides correlates with the therapeutic efficacy of the inhibitor. In a related aspect, the biphasic effect is a function of concentration. In another aspect, the biphasic effect is a function of time.

In a further aspect, the inhibitor is being administered to treat an immunological disorder, a neurological disorder or a hematological disorder.

Exemplary methods and compositions according to this invention are described in greater detail below.

BRIEF DESCRIPTION OF THE DRAWINGS

FIG. 4 demonstrates the FK506 treatment of cells expressing mGluR5 results in time-dependent increase of mGluR5 binding to Homer. HEK293 cells were transfected with pRK5-mGluR5. 1 micromolar FK506 was added to the medium for differing intervals prior to harvesting and preparation of lysates in the indicated buffer, which include inhibitors of phosphatases and proteases. Lysates were mixed with glutathione agarose beads loaded with GST-Homer 3 EVH1 domain for 1 hr at 4 C. mGluR5 that bound to Homer was then analyzed by western blot. Lysates were also assayed to confirm expression of mGluR5 (lower panel). Note the increase in mGluR5 that binds to Homer from lysates of cells treated for 3 hrs or longer with FK506. FK506 treatment did not substantially alter expression of mGluR5.

FIG. 9 shows a sequence comparison of TrpC1 with other Trps which illustrates the conservation of a putative Homer ligand in the C-terminus. Modified from (Wes, 1995) (SEQ ID NO'S:25 to 30). (This should be updated with the largest set of Trp/VR1 family proteins that retain the PXXF [SEQ ID NO:3] motif.)

FIG. 12 shows that Homer binds to two sites in TrpC1. Wild type and the indicated point mutants of TrpC1 were transiently expressed in HEK293 cells and detergent lysates used in binding assays to GSTHomer. Left panels show mutations of the C-terminal Homer binding site while right panels show mutations in the N-terminal Homer binding site. See text for further description of results.

FIG. 18 shows the open reading frame nucleotide coding the sequence (ORF) of a rat Homer protein (SEQ ID NO:6).

FIG. 19 shows the deduced amino acid sequence of rat Homer protein (SEQ ID NO:7).

DETAILED DESCRIPTION OF THE INVENTION

Figure 1:
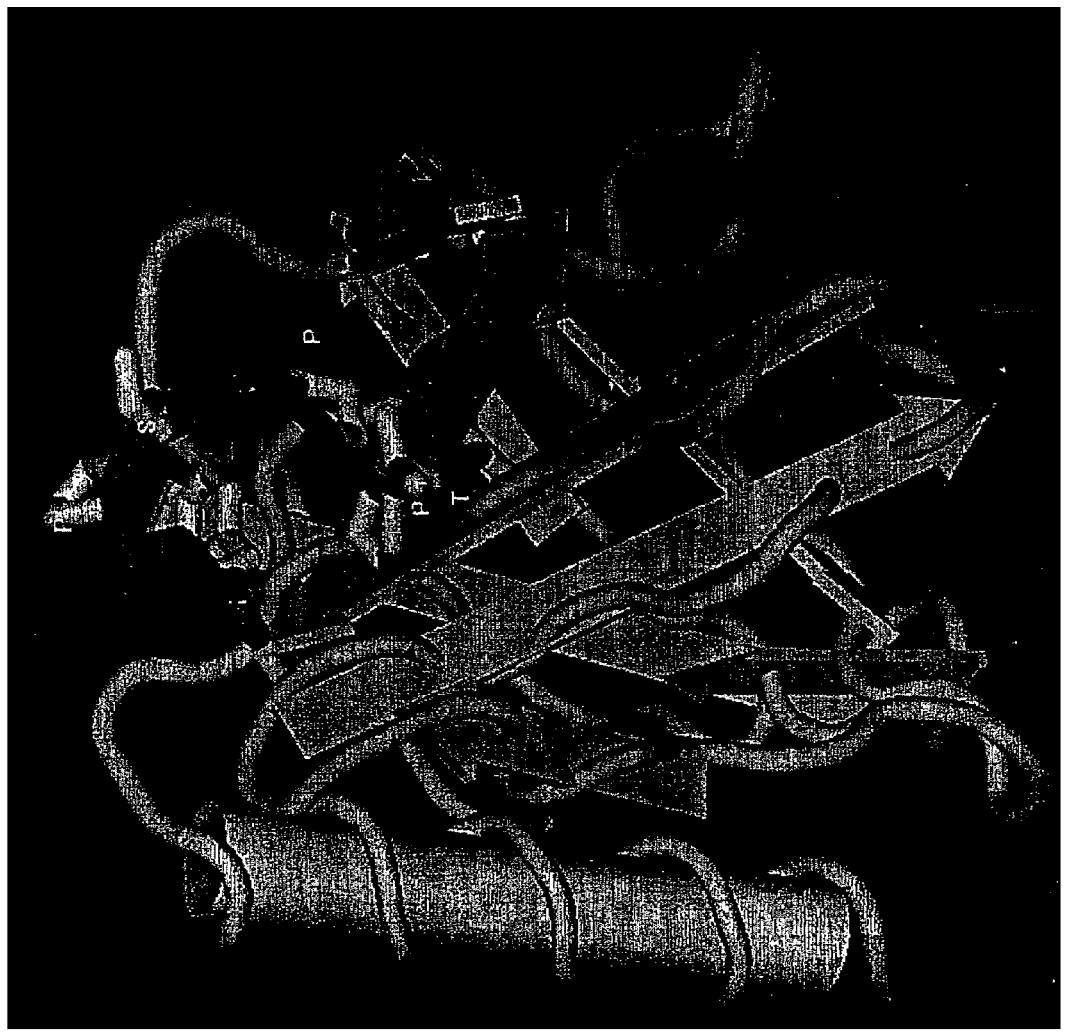
FIG. 1 shows a co-crystal of Homer EVH1 from (Beneken, 2000). The binding surfaces for the second proline and phenylalanine side chains are visualized. The contact for the phenylalanine is unique to the Homer EVH1 domain. The fold is isomorphic to the plextrin homology (PH) domain.
Figure 2:
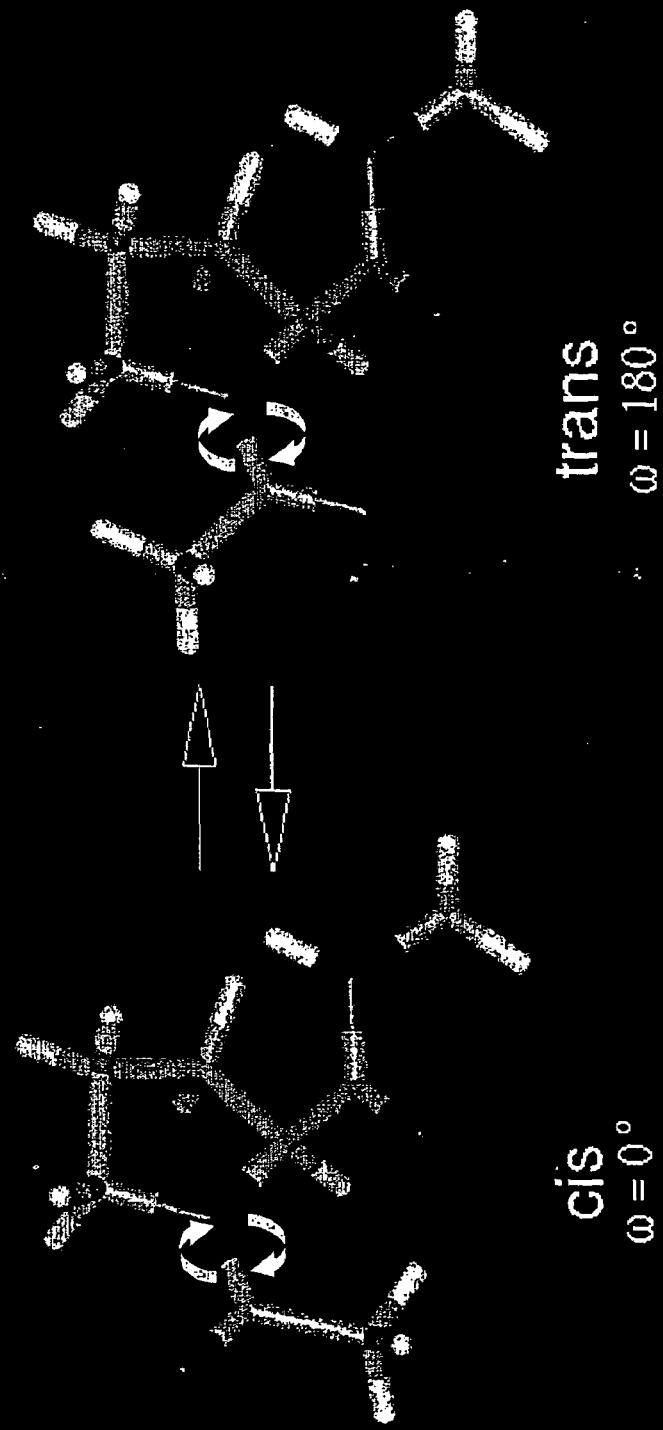
FIG. 2 illustrates that the conformation of the amino acid sequence is restricted at prolines to either cis or trans. Rotation around the peptidyl-prolyl bond involves the breaking and reforming of chemical bonds, and is catalyzed by prolyl isomerases.

Homer binds to proline rich sequences that are present in group 1 metabotropic glutamate receptors, inositol trisphosphate receptors, ryanodine receptors, shank family members, Trp family members, voltage sensitive ion channels and several additional proteins. The present invention demonstrates that Homer's binding and function are dependent upon cistrans peptide prolyl isomerases (PPIase). Like Homer, PPIases bind to proline rich sequences that in many cases appear identical to sequences bound by Homer. PPIases catalyze interconversion of cis trans configurations at the prolyl bond (Gothel and Marahiel, 1999; Schiene and Fischer, 2000). Several classes of compounds have been identified that bind to PPIase enzymes and inhibit their enzyme activity. These compounds are important therapeutically and include FK506, rapamycin and cyclosporin A (Snyder et al., 1998; Steiner et al., 1997). The effect of available compounds on Homer binding indicates a novel pharmacology since binding is enhanced by different classes of rotamase inhibitors including cyclosporin A, GPI 1046, and FK506. None of these agents is optimal since cyclosporin A and FK506 have immunosuppression effects that would limit their general utility. GPI 1046 shows potent enhancement of TrpC1 binding to Homer at 10 nM but the effect decreases with higher doses or longer times. This biphasic effect is anticipated to limit its utility as a modulator of Homer binding.

The systemic actions of these compounds are complex and include, immunosuppression, neuroprotection and induction of neurite outgrowth. While immunosuppression is thought to be due to secondary action of inhibition of calcineurin, actions on neurons are not understood. The data below demonstrate that these compounds alter binding of Homer to its target proteins. Since Homer is an adaptor protein that assembles signaling complexes, the activity of immunophilins of regulating Homer binding can have wide ranging effects of altering neurotransmitter and growth factor signaling, and may rationalize neuroprotective actions of PPIases.

This mechanism of action appears to be due, in part, to a natural competition between Homer and PPIases in binding to proline rich sequences. The PPIase may also be important for establishing the correct conformation of the proline to permit Homer binding. These observations, and described methods, provide a means to identify novel PPIase antagonists with optimal therapeutic activities. Additionally, they validate Homer as an independent target for development of drugs with an anticipated market that parallels and extends PPIase inhibitors.

Before the present invention is described, it is understood that this invention is not limited to the particular methodology, protocols, and reagents described as these may vary. It is also to be understood that the terminology used herein is for the purpose of describing particular embodiments only, and is not intended to limit the scope of the present invention which will be described by the appended claims.

It must be noted that as used herein and in the appended claims, the singular forms "a", "an", and "the" include plural reference unless the context clearly dictates otherwise. Thus, for example, reference to "a subject" includes a plurality of such subjects, reference to "a nucleic acid" includes one or more nucleic acids and equivalents thereof known to those skilled in the art, and so forth.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the methods, devices, and materials are now described. All publications mentioned herein are incorporated herein by reference for the purpose of describing and disclosing the proteins, compounds, and methodologies which are reported in the publications which might be used in connection with the invention. Nothing herein is to be construed as an admission that the invention is not entitled to antedate such disclosure by virtue of prior invention.

As used herein, "biological sample," including grammatical variations thereof, means a sample from an organism and may include, but is not limited to, tissues, bones, hair, urine, stool, blood, organs, and the like.

As used herein, "modulating agents," including grammatical variations thereof, means a chemical composition which varies the binding, activity or function of a Homer protein and would include agonists, antagonists, inverse agonists, competitive and non-competitive inhibitors and cognate ligands.

As used herein, "proline-type Homer consensus ligand," including variations thereof, means an arrangement of amino acid sequences comprising the contiguous motif "PXXF (SEQ ID NO:3)" or "PSSP (SEQ ID NO:4)," denoted as a proline-type 1 Homer ligand consensus sequence and a proline-type 2 ligand consensus sequence, respectively.

An example of a protein containing such proline-type Homer consensus sequence includes, but is not limited to, synphilin (e.g., Acc. No. NP005451, SEQ ID NO:31), EF2kinase (e.g., NP037434, SEQ ID NO:32), p70 (e.g., Acc. No. AAB97097, SEQ ID NO:33), Notch 4 (e.g., NP004548, SEQ ID NO:34), AGE-BP1 (e.g., Q00900, SEQ ID NO:35), cytosolic thymidine kinase (e.g., Acc. No. NP003249, SEQ ID NO:36), neuronal PAS domain protein 2 (e.g., NP840084, SEQ ID NO:37), zona pellucida sperm binding protein 3 precursor (e.g., NP009086, SEQ ID NO:38), Shank family of proteins (e.g., Acc. Nos. Q9JLU4, SEQ ID NO:39; NP113939, SEQ ID NO:40; NP067708, SEQ ID NO:41 Q9WV48, SEQ ID NO:42; P97836, SEQ ID NO:43; AAF61375 SEQ ID NO:44; and AAD29417 SEQ ID NO:45), ryanodine receptor (e.g., Acc. No. NP00053, SEQ ID NO:46), p82 (e.g., Acc. No. AAC50926, SEQ ID NO:47), androgen receptor (e.g., Acc. No. P10275, SEQ ID NO:48), TrpC1 (e.g., Acc. Nos. NP776901, SEQ ID NO:49; NP003295, SEQ ID NO:50; NP057263 SEQ ID NO:51), mGluR1a (e.g., Acc. No. NP000829, SEQ ID NO:52) or mGluR5 (e.g., Acc. No. BAA05891, SEQ ID NO:53).

Sequences for immunophilins and PPIases include, but are not limited to, the following proteins CyA BP (e.g., human, Acc. No. P05092), FKBP59 (e.g., rat, Acc. No. Q9QVC8; human, Acc. No. XP302507), FKBP12.6 (e.g., human, Acc. No. Q16645), FKBP52 (e.g., mouse, P30416; human, Q02790), Pin1 (e.g., human, Q13526), FKB4 (e.g., yeast, Q06205), FKBP54 (e.g., human, Q13451), and FKBP12 (e.g., human, P20071).

As used herein, "neuroprotective agents," including variations thereof, means any chemical composition intended to prevent damage to the brain or spinal cord from ischemia, stroke, convulsions, or trauma. In a related aspect, such agents may be administered before or during an event, but others may be administered some time after.

As used herein, "immunosuppressive agent," including variations thereof, means any chemical composition which has the effect of suppressing the immune system.

As used herein "a competitive agent," including grammatical variations thereof, means a chemical composition that occupies the active site of an enzyme or the binding site of a receptor and prevents a substrate, modulator or ligand from binding. In a related aspect, for example, at sufficiently high concentration of the normal ligand, inhibition is lost. Further, in the presence of such a competitive ligand the Km is altered, but the Vmax remains the same.

As used herein, "biphasic affect," including grammatical variations thereof, means two separate and distinct responses that are separated in time, immediate reaction or quality depending on the concentration and/or temporal administration of an added chemical composition.

As used herein, "synthetic oligopeptide," including grammatical variations thereof, means an artificial peptide of a small number of component amino acids as opposed to a polypeptide. For example, such oligopeptides comprise about from 1 to about 40 amino acids. In a related aspect, such peptides comprise from about 2 to about 30 amino acids in length, from about 3 to 20 amino acids in length or about 4 to 10 amino acids in length.

As used herein, "transformed cell," including grammatical variations thereof, means any cell possessing an altered property that is stably inherited by its progeny.

As used herein, "efficacy," including grammatical variations thereof, means the ability of a drug to effect an illness. For example, efficacy can be used to monitor immunosuppressive therapy and the ability of a drug to provide neuroprotective effects. Further such a functional measure (i.e., efficacy) can be used to measure optimal dose and side effects.

As used herein, "preserving nerve bundles," including grammatical variations thereof, means protecting nerves from injury due to nerve cutting, trauma, or organic deterioration. For example, such injury can include, but is not limited to, stretching the nerve, dissecting a nerve or affecting an area such that blood supply to a nerve is diminished.

As used herein, "Homer signaling related disorders" include, but are not limited to, psoriasis, inflammatory bowel disease (such as Crohn's disease and ulcerative colitis), adult respiratory distress syndrome, dermatitis, meningitis, encephalitis, eczema, asthma and other conditions involving infiltration of T cells and chronic inflammatory responses, skin hypersensitivity reactions, atherosclerosis, leukocyte adhesion deficiency, rheumatoid arthritis, systemic lupus erythematosus (SLE), diabetes mellitus, multiple sclerosis, Reynaud's syndrome, autoimmune thyroiditis, experimental autoimmune encephalomyelitis, Sjorgen's syndrome, juvenile onset diabetes, and immune responses associated with delayed hypersensitivity mediated by cytokines and T-lymphocytes typically found in tuberculosis, sarcoidosis, polymyositis, granulomatosis and vasculitis, pernicious anemia, diseases involving leukocyte diapedesis, CNS inflammatory disorder, multiple organ injury syndrome secondary to septicemia or trauma, autoimmune hemolytic anemia, myasthenia gravis, antigen-antibody complex mediated diseases, and transplantations, including graft vs. host, host vs. graft disease, radical prostatectomy, organ transplantation, trauma, stroke, Alzheimer's disease, Parlinson's disease, amyotrophic lateral sclerosis, lymphoblastic leukemia, acute or chronic myelogenous leukemia, Hodgkin's lymphoma, Non-Hodgkin's lymphoma, myelodysplastic syndrome, multiple myeloma, and chronic lymphocytic leukemia.

Figure 7:
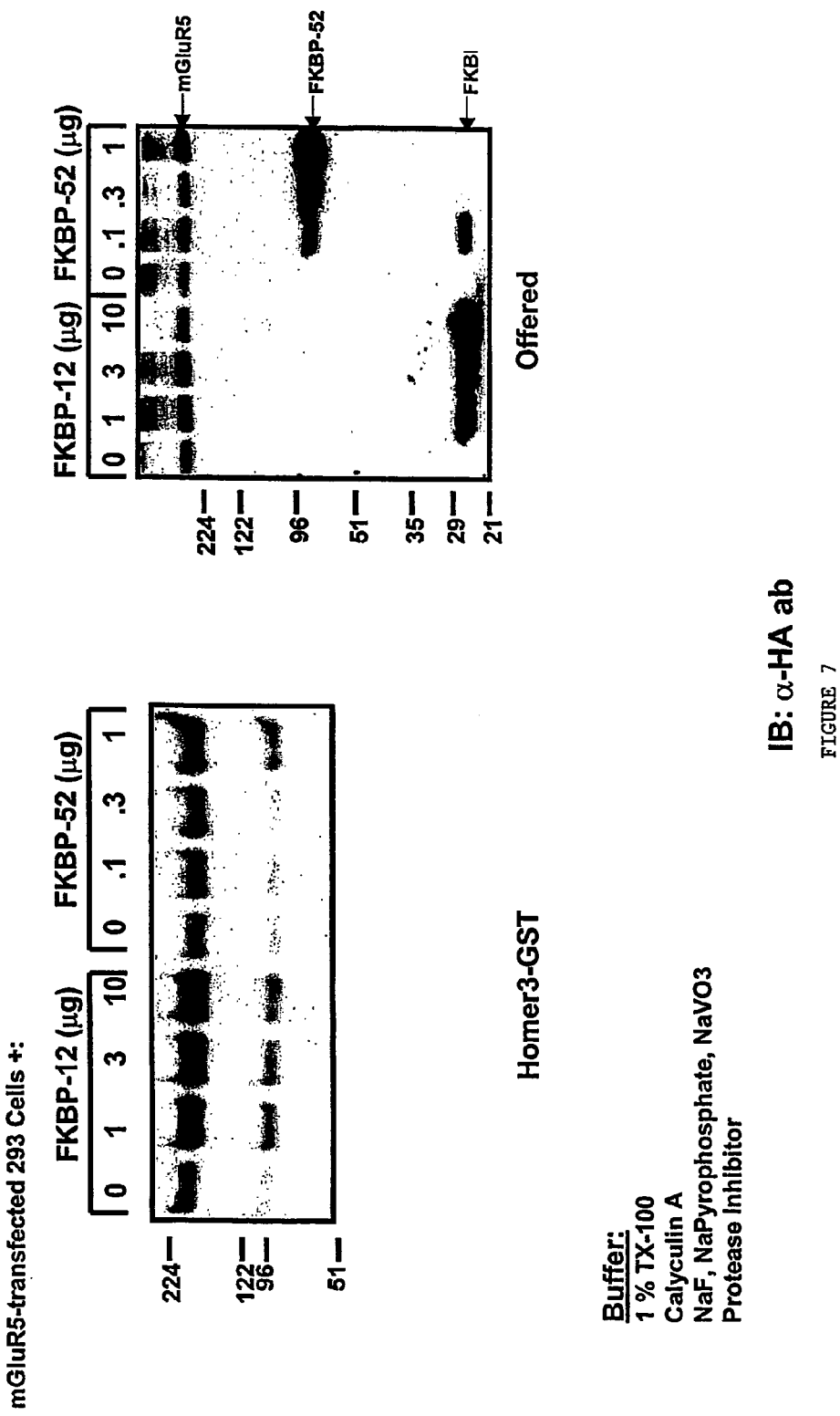
FIG. 7 shows that FKBP12 and FKBP52 co-expression with mGluR5 increases its in vitro binding to GSTHomer. Wild type mGluR5 was co-transfected with FKBP12 or FKBP52 and cell lysates were assayed for binding to GSTHomer. All constructs are tagged with HA epitope and expression of transgenes was confirmed in lysates (right panel). mGluR5 binding increased when co-expressed with FKBP 12 or 52, and greatest binding occurred with highest expression of FKBP protein (left panel).

The nucleotide coding sequence of the Homer protein isolated from rat brain is shown in FIG. 18 as SEQ ID NO:6. The coding sequence has an open reading frame (ORF) of 558 nucleotides (FIG. 18; SEQ ID NO: 6). A 6.5 kb mRNA derived from this DNA encodes a 186 amino acid protein (FIG. 19; SEQ ID NO: 7). A long 3' UTR (Acc. No. U92079) encodes multiple AUUUA (SEQ ID NO:8) repeats, such as have been implicated in mRNA destabilization of immediate early genes (IEG). The amino acid sequence predicts a soluble protein that contains a single GLGF (SEQ ID NO:22) sequence and a preceding arginine (FIG. 7), a so-called "PDZ-like domain" which is predicted to have certain binding properties, based on its characterization in different, unrelated proteins, such as PSD-95.

Additional Homer protein family members can be identified using a differential screening protocol in conjunction with probes based on the sequences described herein, and according to methods well known in the art (See, e.g., U.S. Pat. No. 6,294,355). Alternatively or in addition, such proteins are identified by (i) substantial homology at the nucleotide or protein sequence level to the rat Homer coding sequence or protein, (ii) ability to bind to and affect the activity of effector proteins in the CNS, such as metabotropic glutamate receptors, (iii) binding specificity for a particular binding sequence, and (iv) presence in the sequence of a Homer PDZ-like domain. As implied by its differential expression in stimulated rat brain expression of the gene is stimulated by excitatory synaptic activity (U.S. Pat. No. 6,294,355).

From the present disclosure of the rat Homer coding and polypeptide sequences, identification of additional members of the Homer polypeptide family having substantial homology to Homer can be accomplished by one or more methods known to persons skilled in the art, and discussed below.

For example, using nucleotide probes derived from SEQ ID NO:6, the family members are identified by screening appropriate libraries. In particular, hybridization probes derived from nt 558-nt 1127 of the nearly full length cDNA reported to Genbank (Accession #: U92079) can be synthesized on commercially available DNA synthesizers (e.g., Applied Biosystems Model 381A) using standard techniques well known in the art (Ausubel, et al., 1992). A particularly appropriate library is a CNS or brain library, such as the human brain libraries which are commercially available from Stratagene (La Jolla, Calif.) and InVitrogen (San Diego, Calif.). The probe is typically hybridized at 65° C. and washed at 55° C. (moderate stringency screens). Clones identified by this method are isolated and their coding sequences determined, according to methods known in the art. Clones are further selected if their deduced amino acid sequences minimally include a Homer PDZ-like domain region, as discussed above.

Further characterization of selected clones is carried out by insertion of the isolated coding regions into vectors for expression in an appropriate expression system known in the art. Translated products are then isolated and are tested for ability to bind to specific target proteins in the CNS and binding specificity for a particular peptide binding sequences, including, but not limited to, SSTL (SEQ ID NO:9), SSSL (SEQ ID NO:10), PXXF (SEQ ID NO:3) and PSSP (SEQ ID NO:4).

Further, using the protein sequences presented., e.g., SEQ ID NO: 6 (rat Homer) shown in FIG. 19, as a templates, it is appreciated that additional family members can be identified based on (i) sequence variation between and among the polypeptides and (ii) conservative substitution of amino acids within the sequences.

Moreover, Homer protein sequences may include, but are not limited to, sequences as set forth in the following accession numbers: NP004829, SEQ ID NO:54; NP004830, SEQ ID NO:55; NP004263, SEQ ID NO:56; NP671705, SEQ ID NO:57; NP445762 SEQ ID NO:58; and NP445761 SEQ ID NO:59.

Thus, looking at the N-terminal region of the polypeptides, it is apparent that the first 30 amino acids are invariant among the three sequences. However, positions 31-34 differ. The rat sequence is AVTV (SEQ ID NO:11), while the human and mouse proteins share the sequence GHRF (SEQ ID NO:12). From this variation, it is possible to construct polypeptides in which positions 31-34 have the variable sequences: A/G V/H T/R V/F. Further regions of variability are apparent from inspection of the aligned sequences. Certain regions of the rat Homer protein have been identified as significant in the context of its function. For example, the PDZ-like domain GLGF sequence and preceding arginine at positions 87-90 and 81, respectively, may form a "binding pocket", based on the known binding pocket of the synaptic binding protein PSD95 (Kornau, et al., 1995). In accordance with the foregoing guidelines concerning substitution, this region is invariant among the three exemplified synaptic activation proteins and should therefore be conserved in any sequences deduced from these proteins.

Further substitution at the identified variable positions may be made by making conservative amino acid substitutions. That is, if the two or more of the possible amino acids at a variant position are in a common substitution class, substitution at that position by an amino acid within that class may preserve the conformation and function of the polypeptide. Standard substitution classes that can be used in this analysis are the six classes based on common side chain properties and highest frequency of substitution in homologous proteins in nature, as determined, for example, by a standard Dayhoff frequency exchange matrix (Dayhoff, 1972). These classes are Class I: C; Class II: S, T, P, X A, and G representing small aliphatic side chains and OH-group side chains; Class III: N, Q, D, and C, representing neutral and negatively charged side chains capable of forming hydrogen bonds; Class IV: H, R, and K, representing basic polar side chains; Class V: I, V, and L, representing branched aliphatic side chains, and Met; and Class VI: F, Y, and W, representing aromatic side chains. In addition, each group may include related amino acid analogs, such as ornithine, homoarginine, N-methyl lysine, dimethyl lysine, or trimethyl lysine in class IV, and cyclohexylalanine or a halogenated tyrosine in Group VI. Further, the classes may include both L and D stereoisomers, although L-amino acids are preferred for substitutions.

Polypeptide sequences designed according to the foregoing guidelines can be produced, for example by recombinant expression. The selected ORF is cloned as a fusion with glutathionione-S-transferase (GST) and is express in bacteria. Alternatively, the ORF may be cloned into a mammalian expression vector and expressed in mammalian cells, according to methods known in the art.

In accordance with the present invention, synaptic activation proteins bind cellular components. After determining the cellular binding partner candidate, the synaptic activation protein can be further tested for binding to the candidate in one or more of the in vitro binding assays such as those described below.

For example, the bacterially expressed GST-Homer fusion protein was tested for binding to native mGluR5 in detergent extracts of hippocampus in an in vitro binding assay. mGluR5 binds to GST-Homer fusion protein, but not to GST alone. GST-Homer pull down assays can use purified proteins, recombinant proteins in heterologous cells, native proteins from cell lines or primary cultures or whole animals. For these assays, point mutants of homer (W24A or G89N mutants of Homer 1 or equivalent mutants in Homer 2 or 3) provide informative negative controls (Beneken et al., 2000). Effects on Homer interaction with target proteins can also be assayed by co-immunoprecipitation (co-IP) from the same protein sources (see below).

Assays may also test known or suspected Homer-dependent signaling pathways including: Ca signaling, activation of PLC, activation of MAP kinase, P13kinase, modulation of membrane ion channels, activation of Trp channels, activation of IP3 or RYR channels, and growth factor dependent responses.

Assays can also examine functions of tissues in organ bath or in vivo preparations. These assays are guided by current studies of Homer transgenic mice, which provide insight into organ functions that are dependent on Homer and include: cerebellar function, responses to drugs of addiction, pain and thermal responses, hair color, skeletal or cardiac muscle contraction and pancreatic secretion.

Distinct pharmacologies may be identified for specific therapeutic goals. For example, agents that enhance Homer-dependent signaling and coupling to growth factors may be neuroprotective, while agents that affect homer-dependent coupling to ryanodine receptors could alter cardiac contractility.

The present mechanism as disclosed also indicates that Homer acts in concert with FKBPs and possibly other PPIases. In several experimental models, FKBPs appear to compete with PPIases for binding (see below). Further, it appears that the isomerase activity is important to establish the correct conformation of the target protein for Homer binding. This notion suggests that pharmacological responses to PPIase inhibitors are mediated, in part, by modification of Homer binding. It is therefore anticipated that agents that directly modify Homer binding to its target will be effective for a similar range of conditions. Agents that inhibit PPIases are thought to act by mimicking the proline present in their binding site. Because Homer also binds prolines, it is anticipated that prolylmimetic agents bind to the ligand recognition surface of Homer. Thus, both the physiology and medicinal chemistry may be shared by PPIases and Homer.

Transgenic mouse models can be used to define functions of Homer in calcium-dependent signaling in many tissues, including brain neurons, and it is anticipated that PPIases that regulate Homer binding will have therapeutic actions.

It is important to note that assays of modified Homer binding are distinct from assays of rotamase activity. Homer binds to a specific isomer of the target protein and our assay detects the amount of this protein available to bind Homer. This is a distinct end point from rotamase inhibition. Modulation of Homer binding is the desired physiological end point and so assays of this are valuable and reliable. Based on data using available PPIase inhibitors, it is anticipated that the pharmacology of agents that regulate Homer binding will be distinct from previously reported pharmacology. Moreover, the invention demonstrates that Homer binding to mGluR5 is sensitive to the phosphorylation state of the binding site in mGluR5. This may be coupled to PPIase since activity of certain PPIases is linked to phosphorylation of the target sequence (Lu, 2000).

Another method of assessing binding in vitro is provided by a co-immunoprecipitation assay, in which an antibody directed to one of the proteins is used to assess whether the two proteins form a binding complex in solution. Results of such assays, i.e., testing co-immunoprecipitation of mGluR5 with Homer from hippocampus are demonstrated in Example 7. It can be demonstrated that extracts of hippocampus are immunoprecipitated with either pre-immune serum, anti-Homer serum or anti-Homer serum pretreated with GST-Homer. mGluR5 co-immunoprecipitates with Homer antiserum but not pre-immune serum Additionally, co-immunoprecipitation is blocked by preadsorption of antisera with Homer antigen, indicating the specificity of the antisera for the rat Homer protein.

The potential for natural interaction between the synaptic activation protein and the candidate binding partner can be further assessed in situ and by immunostaining sections of brain tissue with antibodies directed to each of the proteins. The goal of such analysis is to establish that both proteins are expressed in the same regions of the cell. For example, immunostaining experiments of the rat Homer protein with anti-Homer antiserum and immunostaining of mGluR5 with anti-mGluR5 antibodies in adult rat parietal cortex demonstrate that mGluR5 and Homer immunostaining are both enriched in apical dendrites of Layer V pyramidal neurons. These data provide anatomic support for the interaction in vivo between the Homer protein and mGluR5.

The synaptic activation proteins described herein maybe used in screening assays to identify compounds that interfere with or modulate binding of the protein Homer to mGluR5 or mGluR1α, and hence with PI-linked mGluR activity. In accordance with the present invention, compounds identified by this screening assay may be used as drugs for treating epilepsy, abnormal brain development, neural injury, trauma and certain chemical addictions.

Assay formats for measuring the protein-protein interaction are known in the art. For example, purified synaptic activation protein can be coated onto a solid phase, such as a microtiter plate, followed by blocking of open plate binding sites, according to standard methods. mGluR is then added to the plate in the absence or presence of a test compound. Detection of mGluR bound to synaptic activation protein is accomplished by direct labeling of the mGluR or by subsequent addition of a labeled, mGluR-specific binding reagent, such as an antibody. The binding reagent may be radiolabeled, e.g., with $^{125}$I, or may be labeled with a fluorescent dye, an enzyme capable of generating a signal (e.g., horseradish peroxidase), gold or biotin according to methods well know in the art (Howard, 1993). Detection of binding is then carried out using methods appropriate to the signal generated. A test compound is selected for drug development if it significantly alters binding between the proteins.

Accordingly, polynucleotides forming part of the present invention can be used in the large-scale production of PPIase, synaptic activation proteins/proline-type Homer ligands for the described screening assays.

At least two different assay systems, described in the subsections below, can be designed and used as high-throughput screening assays to identify compounds or compositions that modulate or alter Homer protein activity. The screening assays described herein may be used singly or in combination with other assays, including animal models, to identify compounds which modulate Homer protein activity, Homer protein/PPIase interaction and/or Homer protein/proline-type Homer ligand consensus sequence interaction.

The systems described below may be formulated into kits. To this end, Homer protein, either wild type or mutant, or cells expressing Homer protein, either wild type or mutant, can be packaged in a variety of containers, e.g., vials, tubes, microtitre well plates, bottles and the like. Other reagents can be included in separate containers and provided with the kit, e.g., positive controls samples, negative controls samples, proline-type Homer ligand consensus sequence containing peptides and/or proteins, reporter constructs, buffers, cell culture media, etc.

In addition, animal-based systems or models may be used to identify compounds capable of ameliorating symptoms of various disorders. Such animal models may be used as test substrates for the identification of drug pharmaceuticals, therapies and interventions, including compounds, small molecules, ribozymes and antisense molecules that may be effective in treating such disorders. Any compound tested in the high-throughput screening assays as may be tested in animals. In particular, any compound identified in the high-throughput assays as altering Homer protein activity, Homer protein/PPIase interaction and/or Homer protein/proline-type Homer ligand consensus sequence interaction may further be tested in an animal. For example animal models may be exposed to a compound suspected of exhibiting an ability to modulate a Homer signaling pathway, at a sufficient concentration and for a sufficient time to elicit such a modulation of a Homer signaling related disorder in the exposed animals. The response of the animals to the exposure may be monitored by assessing the reversal of symptoms related to Homer signaling or any other way found suitable to assay the effects of such compounds in animals or humans.

In accordance with the invention, a cell-based assay system can be used to screen for compounds that modulate the activity of Homer protein activity, Homer protein/PPIase interaction and/or Homer protein/proline-type Homer ligand consensus sequence interaction. To this end, cells, or lysates thereof, that endogenously express Homer protein, Homer protein/PPIase and/or Homer protein/proline-type Homer ligand consensus sequence, either wild type or mutant, can be used to screen for compounds useful in the alteration or modulation of Homer protein activity, Homer protein/PPIase interaction and/or Homer protein/proline-type Homer ligand consensus sequence interaction. Cells isolated from transgenic animals engineered to express Homer protein, Homer protein/PPIase and/or Homer protein/proline-type Homer ligand consensus sequence or primary cells expressing Homer protein, Homer protein/PPIase and/or Homer protein/proline-type Homer ligand consensus sequence isolated from animal or human tissue may be used for screening purposes. Alternatively, cell lines genetically engineered to express Homer protein, PPIase and/or a proline-type Homer ligand consensus sequence, or lysates thereof, may be used for screening purposes. In one embodiment, host cells genetically engineered to express a functional Homer protein, PPIase and/or a proline-type Homer ligand consensus sequence or lysates thereof, may be used for screening purposes.

In utilizing such cell systems, the cells expressing Homer protein, PPIase and/or a proline-type Homer ligand consensus sequence are exposed to a test compound or to vehicle controls (e.g., placebos). After exposure, the cells can then be assayed, for example, to measure the expression and/or activity of components of the signal transduction pathway of the Homer protein, or the activity of the signal transduction pathway itself can be assayed. In this regard, any intermediate step in the signal transduction pathway can be measured or assayed to determine the effect of the test compound on the activity of Homer protein activity, Homer protein/PPIase interaction and/or Homer protein/proline-type Homer ligand consensus sequence interaction in/on the signal transduction pathway. For example, after exposure, cell lysates can be assayed for modulation of $Ca^{+2}$ signaling, modulation of PLC, modulation of Trp channels, modulation of MAP kinase, modulation of PI3kinase, modulation of ion channels, modulation of IP3 channels, modulation of RYR channels, and modulation of growth factor dependent responses by means well known in the art. Such assays provide a simple, sensitive, easily automatable detection system for pharmaceutical screening.

In addition to cell based assays, non-cell based assay systems may be used to identify compounds that regulate or alter the Homer protein activity, Homer protein/PPIase interaction and/or Homer protein/proline-type Homer ligand consensus sequence interaction. In accordance with the invention, recombinantly expressed Homer protein, PPIase and/or proline-type Homer ligand consensus sequence, including phosphorylated Homer protein, PPIase and/or a proline-type Homer ligand consensus sequence, or cell lysates obtained from cells that express such products may be used in the screening assays described herein. Such compounds may act as agonists or antagonists of Homer protein activity, Homer protein/PPIase interaction and/or Homer protein/proline-type Homer ligand consensus sequence interaction and may be used in the treatment of Homer signaling related disorders.

Isolated membranes may be used to identify compounds that interact with Homer protein. For example, in a typical experiment using isolated membranes, 293 cells may be genetically engineered to express the Homer protein, PPIase and/or proline-type Homer ligand consensus sequences. Membranes can be harvested by standard techniques and used in an in vitro binding assay, e.g., specific binding is determined by comparison with binding assays performed in the presence of excess unlabeled ligand.

In one approach to screening assays, Homer protein fragments, PPIase fragments and/or proline-type Homer ligand consensus sequences are displayed on the surface of a cell or viral particle, and the ability of particular cells or cell-lysate products via the displayed product is detected in a "panning assay". For example, the gene library can be cloned into the gene for a surface membrane protein of a bacterial cell, and the resulting fusion protein detected by panning (Ladner et al., WO 88/06630; Fuchs et al. (1991) Bio/Technology 9:1370-1371; and Goward et al. (1992) TIBS 18:136-140).

A gene library can be expressed as a fusion protein on the surface of a viral particle. For instance, in the filamentous phage system, foreign peptide sequences can be expressed on the surface of infectious phage, thereby conferring two significant benefits. First, since these phage can be applied to affinity matrices at concentrations well over $10^{13}$ phage per milliliter, a large number of phage can be screened at one time. Second, since each infectious phage displays a gene product on its surface, if a particular phage is recovered from an affinity matrix in low yield, the phage can be amplified by another round of infection. The group of almost identical *E. coli* filamentous phages M13, fd, and f1 are most often used in phage display libraries. Either of the phage gIII or gVIII coat proteins can be used to generate fusion proteins without disrupting the ultimate packaging of the viral particle. Foreign epitopes can be expressed at the $NH_2$-terminal end of pIII and phage bearing such epitopes recovered from a large excess of phage lacking this epitope (Ladner et al. PCT publication WO 90/02909; Garrard et al., PCT publication WO 92/09690; Marks et al. (1992) J. Biol. Chem. 267:16007-16010; Griffiths et al. (1993) EMBO J 12:725-734; Clackson et al. (1991) Nature 352:624-628; and Barbas et al. (1992) PNAS 89:4457-4461).

A common approach uses the maltose receptor of *E. coli* (the outer membrane protein, LamB) as a peptide fusion partner (Charbit et al. (1986) EMBO 5, 3029-3037). Oligonucleotides have been inserted into plasmids encoding the LamB gene to produce peptides fused into one of the extracellular loops of the protein. These peptides are available for binding to Homer protein, PPIase and/or proline-type Homer ligand consensus sequences. Other cell surface proteins, e.g., OmpA (Schorr et al. (1991) Vaccines 91, pp. 387-392), PhoE (Agterberg, et al. (1990) Gene 88, 37-45), and PAL (Fuchs et al. (1991) Bio/Tech 9, 1369-1372), as well as large bacterial surface structures have served as vehicles for peptide display. Peptides can be fused to pilin, a protein which polymerizes to form the pilus-a conduit for interbacterial exchange of genetic information (Thiry et al. (1989) Appl. Environ. Microbiol. 55, 984-993). Because of its role in interacting with other cells, the pilus provides a useful support for the presentation of peptides to the extracellular environment. Another large surface structure used for peptide display is the bacterial motive organ, the flagellum. Fusion of peptides to the subunit protein flagellin offers a dense array of many peptides copies on the host cells (Kuwajima et al. (1988) Bio/Tech. 6, 1080-1083). Surface proteins of other bacterial species have also served as peptide fusion partners. Examples include the Staphylococcus protein A and the outer membrane protease IgA of Neisseria (Hansson et al. (1992) J. Bacteriol. 174, 4239-4245 and Klauser et al. (1990) EMBO J. 9, 1991-1999).

In the filamentous phage systems and the LamB system described above, the physical link between the peptide and its encoding DNA occurs by the containment of the DNA within a particle (cell or phage) that carries the peptide on its surface. Capturing the peptide captures the particle and the DNA within. An alternative scheme uses the DNA-binding protein LacI to form a link between peptide and DNA (Cull et al. (1992) PNAS USA 89:1865-1869). This system uses a plasmid containing the LacI gene with an oligonucleotide cloning site at its 3'-end. Under the controlled induction by arabinose, a LacI-peptide fusion protein is produced. This fusion retains the natural ability of LacI to bind to a short DNA sequence known as LacO operator (LacO). By installing two copies of LacO on the expression plasmid, the LacI-peptide fusion binds tightly to the plasmid that encoded it. Because the plasmids in each cell contain only a single oligonucleotide sequence and each cell expresses only a single peptide sequence, the peptides become specifically and stably associated with the DNA sequence that directed its synthesis. The cells of the library are gently lysed and the peptide-DNA complexes are exposed to a matrix of immobilized receptor to recover the complexes containing active peptides. The associated plasmid DNA is then reintroduced into cells for amplification and DNA sequencing to determine the identity of the peptide ligands. As a demonstration of the practical utility of the method, a large random library of dodecapeptides was made and selected on a monoclonal antibody raised against the opioid peptide dynorphin B. A cohort of peptides was recovered, all related by a consensus sequence corresponding to a six-residue portion of dynorphin B. (Cull et al. (1992) Proc. Natl. Acad. Sci. U.S.A. 89-1869).

This scheme, sometimes referred to as peptides-on-plasmids, differs in two important ways from the phage display methods. First, the peptides are attached to the C-terminus of the fusion protein, resulting in the display of the library members as peptides having free carboxy termini. Both of the filamentous phage coat proteins, pIII and pVIII, are anchored to the phage through their C-termini, and the guest peptides are placed into the outward-extending N-terminal domains. In some designs, the phage-displayed peptides are presented right at the amino terminus of the fusion protein. (Cwirla, et al. (1990) Proc. Natl. Acad. Sci. U.S.A. 87, 6378-6382). A second difference is the set of biological biases affecting the population of peptides actually present in the libraries. The LacI fusion molecules are confined to the cytoplasm of the host cells. The phage coat fusions are exposed briefly to the cytoplasm during translation but are rapidly secreted through the inner membrane into the periplasmic compartment, remaining anchored in the membrane by their C-terminal hydrophobic domains, with the N-termini, containing the peptides, protruding into the periplasm while awaiting assembly into phage particles. The peptides in the LacI and phage libraries may differ significantly as a result of their exposure to different proteolytic activities. The phage coat proteins require transport across the inner membrane and signal peptidase processing as a prelude to incorporation into phage. Certain peptides exert a deleterious effect on these processes and are underrepresented in the libraries (Gallop et al. (1994) J. Med. Chem. 37(9):1233-1251). These particular biases are not a factor in the LacI display system.

The number of small peptides available in recombinant random libraries is enormous. Libraries of $10^7$-$10^9$ independent clones are routinely prepared. Libraries as large as $10^{11}$ recombinants have been created, but this size approaches the practical limit for clone libraries. This limitation in library size occurs at the step of transforming the DNA containing randomized segments into the host bacterial cells. To circumvent this limitation, an in vitro system based on the display of nascent peptides in polysome complexes has recently been developed. This display library method has the potential of producing libraries 3-6 orders of magnitude larger than the currently available phage/phagemid or plasmid libraries. Furthermore, the construction of the libraries, expression of the peptides, and screening, is done in an entirely cell-free format.

The specific role of the Homer protein in vivo can be investigated by engineering Homer "knock out" mice in which most of the endogenous Homer gene coding sequence is deleted, thereby creating mice which are unable to produce functional Homer protein.

To this end, transgenic animals that express the Homer protein, PPIase and/or proline-type Homer ligand consensus sequences can be used. Animals of any species, including, but not limited to, mice, rats, rabbits, guinea pigs, pigs, micropigs, goats, and non-human primates, e.g., baboons, monkeys, and chimpanzees may be used to generate Homer protein transgenic animals.

Any technique known in the art may be used to introduce the human Homer protein transgene into animals to produce the founder lines of transgenic animals. Such techniques include, but are not limited to pronuclear microinjection (Hoppe, P. C. and Wagner, 1989, U.S. Pat. No. 4,873,191);

retrovirus mediated gene transfer into germ lines (Van der Putten et al., 1985, Proc. Natl. Acad. Sci., USA 82: 6148-6152); gene targeting in embryonic stem cells (Thompson et al., 1989, Cell 56: 313-321); electroporation of embryos (Lo, 1983, Mol Cell. Biol. 3: 1803-1814); and sperm-mediated gene transfer (Lavitrano et al., 1989, Cell 57: 717-723); etc. For a review of such techniques, see Gordon, 1989, Transgenic Animals, Intl. Rev. Cytol. 115: 171-229, which is incorporated by reference herein in its entirety.

In one embodiment, transgenic animals carry the Homer transgene in all their cells, in another embodiment, animals carry the transgene in some, but not all their cells, i.e., mosaic animals. The transgene may be integrated as a single transgene or in concatamers, e.g., head-to-head tandems or head-to-tail tandems. The transgene may also be selectively introduced into and activated in a particular cell type by following, for example, the teaching of Lasko et al. (Lasko, M. et al., 1992, Proc. Natl. Acad. Sci. USA 89: 6232-6236). The regulatory sequences required for such a cell-type specific activation will depend upon the particular cell type of interest, and will be apparent to those of skill in the art. When it is desired that the Homer transgene be integrated into the chromosomal site of the endogenous Homer gene, gene targeting is preferred. Briefly, when such a technique is to be utilized, vectors containing nucleotide sequences homologous to the endogenous Homer gene and/or sequences flanking the gene are designed for the purpose of integrating, via homologous recombination with chromosomal sequences, into and disrupting the function of the endogenous Homer gene. The transgene may also be selectively expressed in a particular cell type with concomitant inactivation of the endogenous Homer gene in only that cell type, by following, for example, the teaching of Gu et al. (Gu, et al., 1994, Science 265: 103-106). The regulatory sequences required for such a cell-type specific recombination will depend upon the particular cell type of interest, and will be apparent to those of skill in the art.

Once founder animals have been generated, standard techniques such as Southern blot analysis or PCR techniques are used to analyze animal tissues to determine whether integration of the transgene has taken place. The level of mRNA expression of the transgene in the tissues of the founder animals may also be assessed using techniques which include but are not limited to Northern blot analysis of tissue samples obtained from the animal, in situ hybridization analysis, and RT-PCR. Samples of Homer gene-expressing tissue, may also be evaluated immunocytochemically using antibodies specific for the Homer transgene product.

The compounds that are determined to affect Homer protein activity, Homer protein/PPIase interaction and/or Homer protein/proline-type Homer ligand consensus sequence interaction can be administered to a patient at therapeutically effective doses to treat or ameliorate Homer signaling related disorders. A therapeutically effective dose refers to that amount of the compound sufficient to result in amelioration of symptoms of Homer signaling related disorder (e.g., restoring erectile function).

The assays described above can identify compounds which affect Homer protein activity, Homer protein/PPIase interaction and/or Homer protein/proline-type Homer ligand consensus sequence interaction. For example, compounds that affect Homer protein activity include but are not limited to compounds that bind to the Homer protein, inhibit binding of the natural ligand, and either activate signal transduction (agonists) or block activation (antagonists), and compounds that bind to the natural ligand of the Homer protein and neutralize ligand activity. However, it should be noted that the assays described can also identify compounds that modulate Homer signaling pathways (e.g., compounds which affect. downstream signaling events, such as inhibitors or enhancers of G protein activities which participate in transducing the signal activated by ligand binding to the Homer protein). The identification and use of such compounds which affect signaling events downstream of Homer protein binding and thus modulate effects of Homer protein are within the scope of the invention.

The compounds which may be screened in accordance with the invention include, but are not limited to peptides, antibodies and fragments thereof, and other organic compounds (e.g., peptidomimetics) that bind to the Homer protein, PPIase and/or proline-type Homer ligand consensus sequences and either mimic the activity triggered by the natural ligand (i.e., agonists) or inhibit the activity triggered by the natural ligand (i.e., antagonists); as well as peptides, antibodies or fragments thereof, and other organic compounds that include the Homer protein, PPIase and/or proline-type Homer ligand consensus sequences (or portions thereof) that bind to and "neutralize" natural ligand.

Compounds may include, but are not limited to, peptides such as, for example, soluble peptides, including but not limited to members of random peptide libraries; (see, e.g., Lam, K. S. et al., 1991, Nature 354: 82-84; Houghten, R. et al., 1991, Nature 354: 84-86), and combinatorial chemistry-derived molecular library made of D- and/or L-configuration amino acids, phosphopeptides (including, but not limited to, members of random or partially degenerate, directed phosphopeptide libraries; see, e.g., Songyang, Z. et al., 1993, Cell 72: 767-778), antibodies (including, but not limited to, polyclonal, monoclonal, humanized, anti-idiotypic, chimeric or single chain antibodies, and FAb, F(ab')$^2$ and FAb expression library fragments, and epitope-binding fragments thereof), and small organic or inorganic molecules.

Other compounds which can be screened in accordance with the invention include but are not limited to small organic molecules that are able to cross the blood-brain barrier, gain entry into an appropriate cell and affect the expression of the Homer protein or some other gene involved in the Homer signaling pathway (e.g., by interacting with the regulatory region or transcription factors involved in gene expression); or such compounds that affect the activity of the Homer protein or the activity of some other intracellular factor involved in the Homer signaling pathway.

Computer modeling and searching technologies permit identification of compounds, or the improvement of already identified compounds, that can modulate Homer protein activity, Homer protein/PPIase interaction and/or Homer protein/proline-type Homer ligand consensus sequence interaction. Having identified such a compound or composition, the active sites or regions are identified. Such active sites might typically be ligand binding sites. The active site can be identified using methods known in the art including, for example, from the amino acid sequences of peptides, from the nucleotide sequences of nucleic acids, or from study of complexes of the relevant compound or composition with its natural ligand. In the latter case, chemical or X-ray crystallographic methods can be used to find the active site by finding where on the factor the complexed ligand is found.

Next, the three dimensional geometric structure of the active site is determined. This can be done by known methods, including X-ray crystallography, which can determine a complete molecular structure. On the other hand, solid or liquid phase NMR can be used to determine certain intramolecular distances. Any other experimental method of structure determination can be used to obtain partial or complete geometric structures. The geometric structures may be measured with a complexed ligand, natural or artificial, which may increase the accuracy of the active site structure determined.

If an incomplete or insufficiently accurate structure is determined, the methods of computer based numerical modeling can be used to complete the structure or improve its accuracy. Any recognized modeling method may be used, including parameterized models specific to particular biopolymers such as proteins or nucleic acids, molecular dynamics models based on computing molecular motions, statistical mechanics models based on thermal ensembles, or combined models. For most types of models, standard molecular force fields, representing the forces between constituent atoms and groups, are necessary, and can be selected from force fields known in physical chemistry. The incomplete or less accurate experimental structures can serve as constraints on the complete and more accurate structures computed by these modeling methods.

Finally, having determined the structure of the active site, either experimentally, by modeling, or by a combination, candidate modulating compounds can be identified by searching databases containing compounds along with information on their molecular structure. Such a search seeks compounds having structures that match the determined active site structure and that interact with the groups defining the active site. Such a search can be manual, but is preferably computer assisted. These compounds found from this search are potential Homer protein modulating compounds.

Alternatively, these methods can be used to identify improved modulating compounds from an already known modulating compound or ligand. The composition of the known compound can be modified and the structural effects of modification can be determined using the experimental and computer modeling methods described above applied to the new composition. The altered structure is then compared to the active site structure of the compound to determine if an improved fit or interaction results. In this manner systematic variations in composition, such as by varying side groups, can be quickly evaluated to obtain modified modulating compounds or ligands of improved specificity or activity.

Further experimental and computer modeling methods useful to identify modulating compounds based upon identification of the active sites of Homer protein, and related signaling, will be apparent to those of skill in the art.

Examples of molecular modeling systems are the CHARMm and QUANTA programs (Polygen Corporation, Waltham, Mass.). CHARMm performs the energy minimization and molecular dynamics functions. QUANTA performs the construction, graphic modeling and analysis of molecular structure. QUANTA allows interactive construction, modification, visualization, and analysis of the behavior of molecules with each other.

A number of articles review computer modeling of drugs interactive with specific proteins, such as Rotivinen, et al. (1988 Acta Pharmaceutical Fennica 97: 159-166); Ripka (1988 New Scientist 54-57); McKinaly and Rossmann (1989, Annu. Rev. Pharmacol. Toxiciol. 29: 111-122); Perry and Davies, OSAR: Quantitative Structure-Activity Relationships in Drug Design pp. 189-193 Alan R. Liss, Inc. 1989; Lewis and Dean (1989, Proc. R. Soc. Lond. 236: 125-140 and 141-162); and, with respect to a model receptor for nucleic acid components, Askew, et al. (1989, J. Am. Chem. Soc. 111: 1082-1090). Other computer programs that screen and graphically depict chemicals are available from companies such as BioDesign, Inc. (Pasadena, Calif.), Allelix, Inc. (Mississauga, Ontario, Canada), and Hypercube, Inc. (Cambridge, Ontario).

Although described above with reference to design and generation of compounds which could alter binding, one could also screen libraries of known compounds, including natural products or synthetic chemicals, and biologically active materials, including proteins, for compounds which are inhibitors or activators.

Compounds identified via assays such as those described herein may be useful, for example, in elaborating the biological function of the Homer protein. Assays for testing the efficacy of compounds identified in the cellular screen can be tested in animal model systems. Such animal models may be used as test substrates for the identification of drugs, pharmaceuticals, therapies and interventions which may be effective in treating Homer signaling disorders.

Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds which exhibit large therapeutic indices are preferred. While compounds that exhibit toxic side effects may be used, care should be taken to design a delivery system that targets such compounds to the site of affected tissue in order to minimize potential damage to unaffected cells and, thereby, reduce side effects.

The data obtained from the cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

Pharmaceutical compositions for use in accordance with the present invention may be formulated in a conventional manner using one or more physiologically acceptable carriers or excipients.

Thus, the compounds and their physiologically acceptable salts and solvates may be formulated for administration by inhalation or insufflation (either through the mouth or the nose) or oral, buccal, parenteral or rectal administration.

For oral administration, the pharmaceutical compositions may take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents as appropriate.

Preparations for oral administration may be suitably formulated to give controlled release of the active compound.

For buccal administration the compositions may take the form of tablets or lozenges formulated in conventional manner.

For administration by inhalation, the compounds for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g., gelatin for use in an inhaler or insufflator may be formulated containing a powder mix of the compound and a suitable powder base such as lactose or starch.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration.

The peptide agents of the invention can be prepared using standard solid phase (or solution phase) peptide synthesis methods, as is known in the art. In addition, the DNA encoding these peptides may be synthesized using commercially available oligonucleotide synthesis instrumentation and produced recombinantly using standard recombinant production systems. The production using solid phase peptide synthesis is necessitated if non-gene-encoded amino acids are to be included.

The following examples are intended to illustrate but not limit the invention.

EXAMPLE 1

PPIase Regulation of Homer Binding

Figure 3:
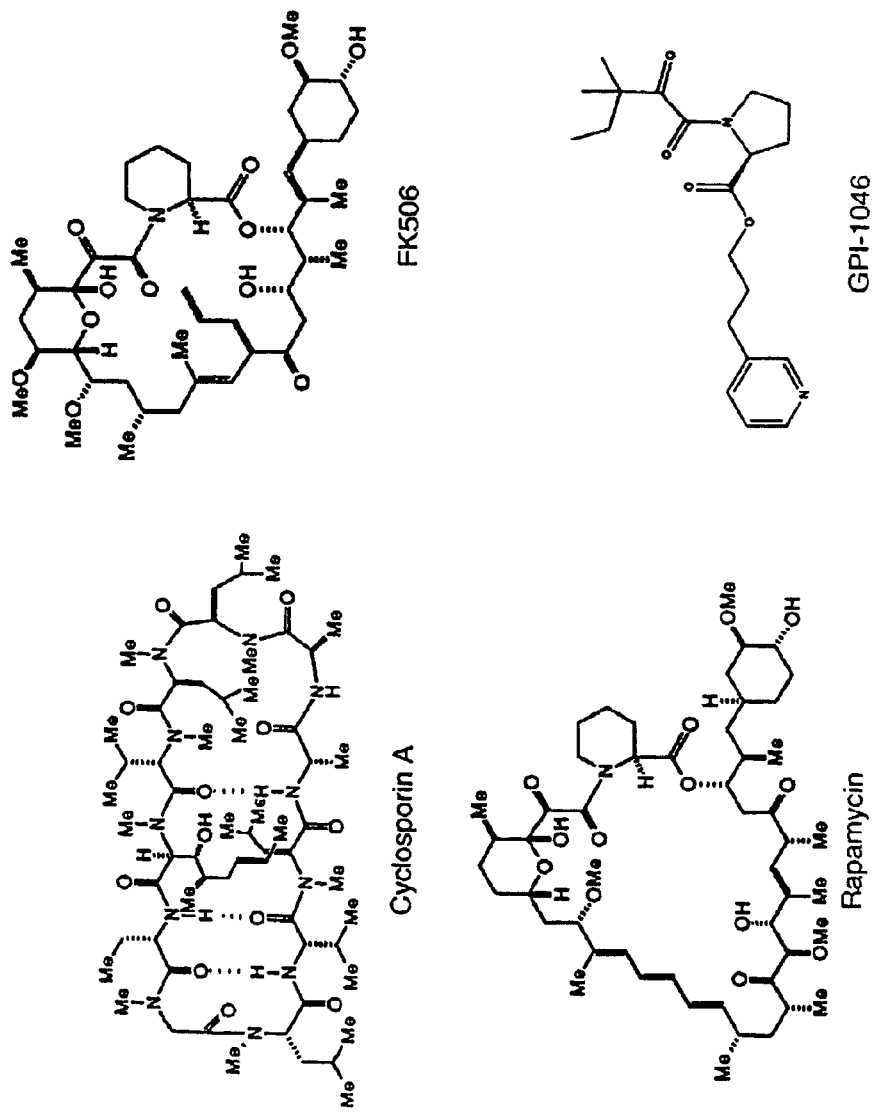
FIG. 3 shows the chemical structures of the four classes of PPIase inhibitors. Modified from (Snyder, 1998).

As a first test of the hypothesis, the effect of treating cells expressing mGluR5 transgene with agents that bind to and inactivate PPIases was examined. There are three families of rotamases expressed in mammalian tissues that possess distinct structures and pharmacologies. The FKBP family includes FKBP 12, 12.6, 13, 25, 33, 51 and 52, and members of this family are inhibited by FK506 (Gothel and Marahiel, 1999) (FIG. 3). The Cyclophilin family includes cyclophilin A-D and cyclophilin 40, and members of this family are inhibited by cyclosporin A (Gothel and Marahiel, 1999). The Pin family is a newly described group of PPIases (Lu et al., 1996) of the parvulin family (Gothel and Marahiel, 1999). Pin1 does not have a reported pharmacology of antagonists.

FK506 is a useful pharmacological tool to inhibit FKBP rotamase activity, but also possesses other actions that complicate analysis. After binding to FK506, FKBP binds to the phosphatase termed calcineurin and inhibits its activity (Gothel and Marahiel, 1999). Recently, new pharmacological agents have been developed that bind to FKBP and inhibit its activity, but do not affect calcineurin activity (Snyder et al., 1998). GPI 1046 is representative of this class of FKBP antagonist (FIG. 3).

If PPIases regulate the conformational state of the mGluR5, it was anticipated that PPIase inhibitors would alter the ability of the mGluR5 to bind to Homer. To examine this hypothesis, Homer was expressed as a bacterial fusion protein with glutathione S-transferase (GST) and loaded the protein on a glutathione agarose bead. These binding assays are identical to those used previously to document the ligand consensus sequence in mGluR5 (Tu et al., 1998), and for analysis of the binding surfaces of Homer (Beneken et al., 2000).

Cells were treated for different times with PPIase inhibitors and then harvested in buffer containing protease and phosphatase inhibitors and 1% Triton detergent. Soluble lysates were then mixed with beads loaded with GST-Homer incubated for 1 hr at 4° C., washed several times and proteins eluted with SDS loading buffer. Treatment of cells with 1 micromolar FK506 resulted in a time-dependent increase in mGluR5 binding (FIG. 4). Increased binding was detected by 3 hrs and remained elevated for 24 hrs.

Figure 5:
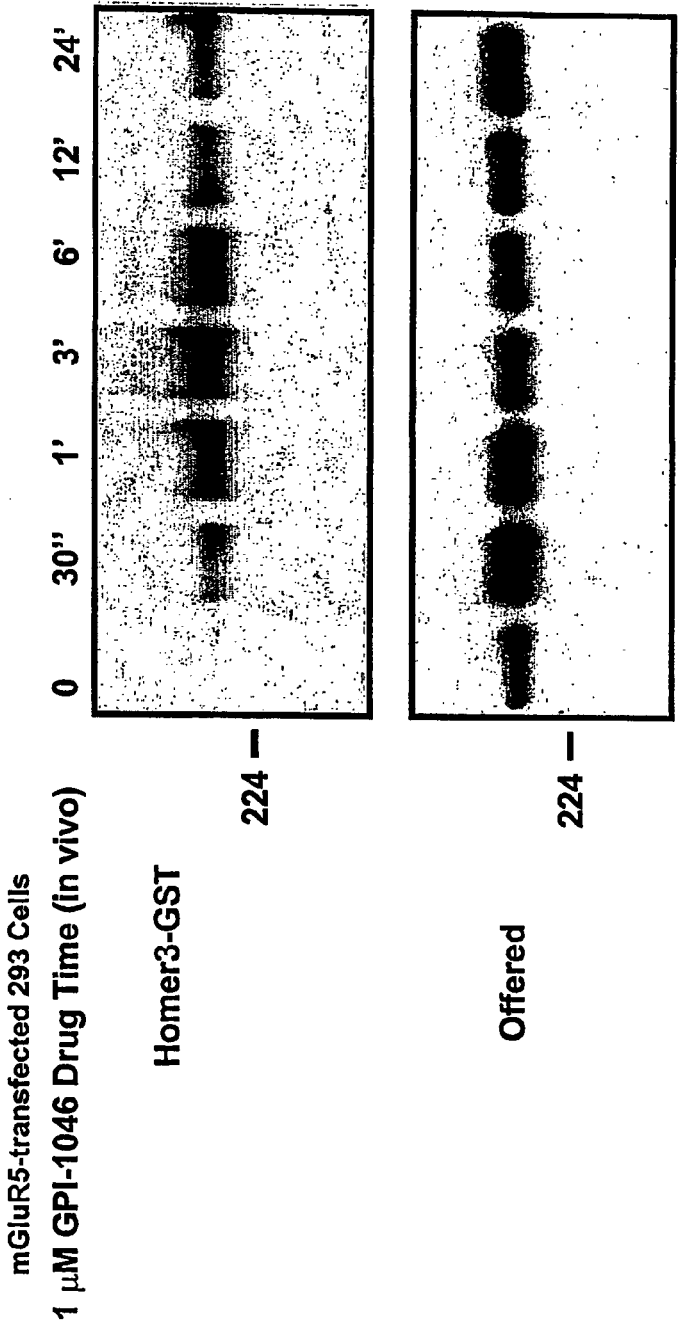
FIG. 5 shows that GPI1046 treatment of HEK293 cells that express mGluR5 results in time-dependent increase of mGluR5 binding to Homer. The experiment is identical to FIG. 4 with the exception that cells were treated with 1 micromolar GPI-1046.

The pharmacology of the response was next examined by treating cells with GPI1046, which inhibits FKBP 12 and 12.6 but does not inhibit calcineurin (Snyder et al., 1998). 1 micromolar GPI 1046 was also effective in increasing mGluR binding to GST-Homer (FIG. 5). This result suggests that the increase in mGluR5 binding is due to inhibition of PPIase rather than calcineurin. In contrast to FK506, mGluR5 binding increased within 30 min, peaked by 3 hrs and decreased after 12 or 24 hrs of treatment GPI 1046 did not significantly alter expression of mGluR5.

Figure 6:
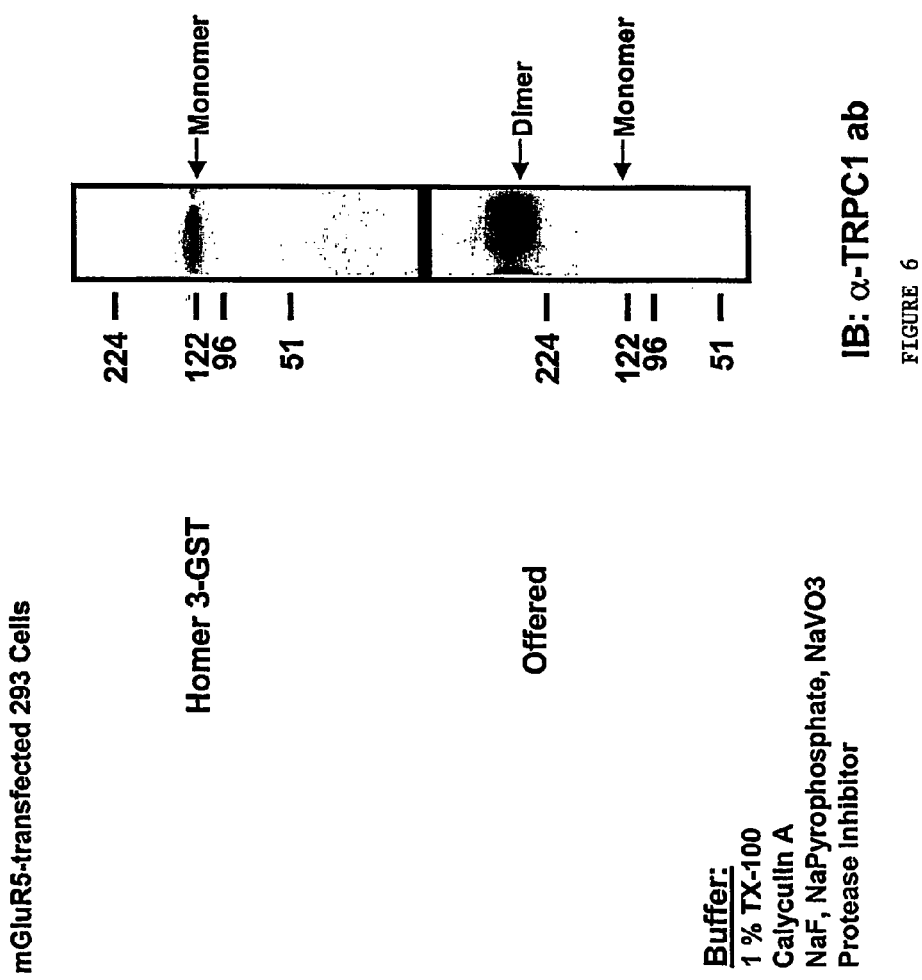
FIG. 6 shows that FKBP52 binds mGluR5. mGluR5 was expressed in HEK293 cells and lysates were assayed for binding to GST-FKBP52. Note FKBP52 binds mGluR5 monomeric form preferentially while the major form in lysate is dimer.

One mechanism that would explain increased mGluR5 binding by FK506 and GPI1046 is that endogenous PPIase binds to and occludes the Homer ligand. Since PPIases also bind proline rich sequences, it is possible that Homer and PPIases bind and compete for the same proline-rich sequence. Therefore, whether mGluR5 would bind to GST-FKBP12 or the related FKBP52 was examined. Lysates were prepared from cells expressing mGluR5 and used for binding assays as described above. mGluR5 bound to GST-FKBP52 (FIG. 6), but not to FKBP12. This is the first demonstration of this interaction.

To further examine the hypothesis that Homer binding is modified by FKBPs, the consequence of co-expressing mGluR5 and FKBP12 or FKBP52 on the ability of the mGluR5 to subsequently bind GST-Homer was examined. In these assays, both FKBP12 and FKBP52 increased binding to GST-Homer (FIG. 7) without altering expression of mGluR5. Because all transgenes are tagged with the HA epitope, it is possible to compare the relative efficacy of FKBP12 and FKBP52. In these assays, FKBP52 appeared equally effective with FKBP12. This result suggests that the FKBP increases the pool of mGluR5 in the optimal configuration/state to bind Homer.

EXAMPLE 2

Homer Binds to Trp Family Protein TrpC1

Figure 8:
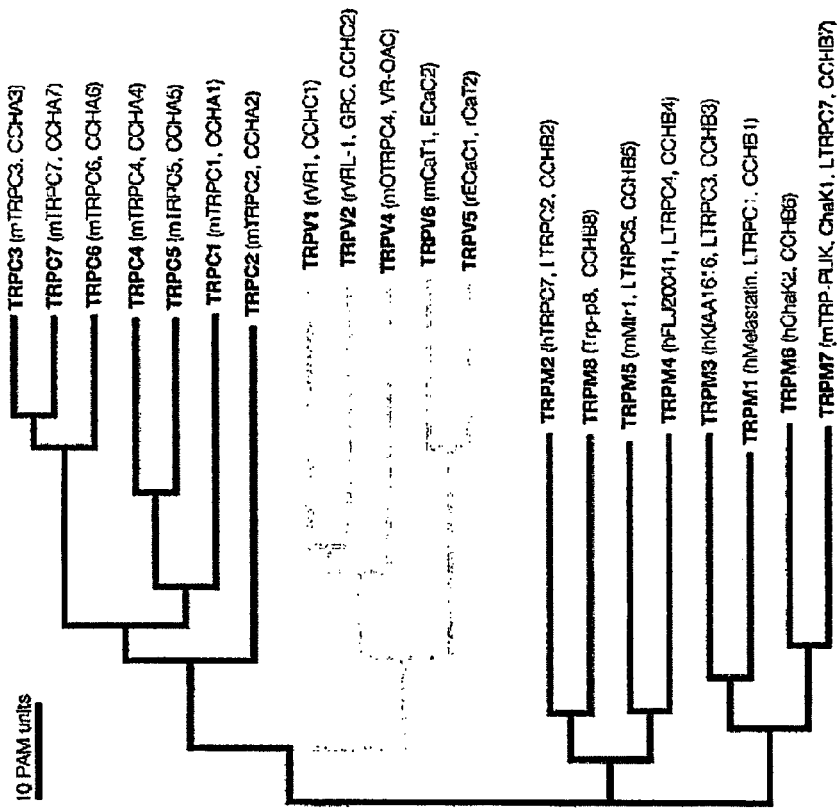
FIG. 8 illustrates the family of Trp related proteins (from Clapham, 2001)
Figure 9:
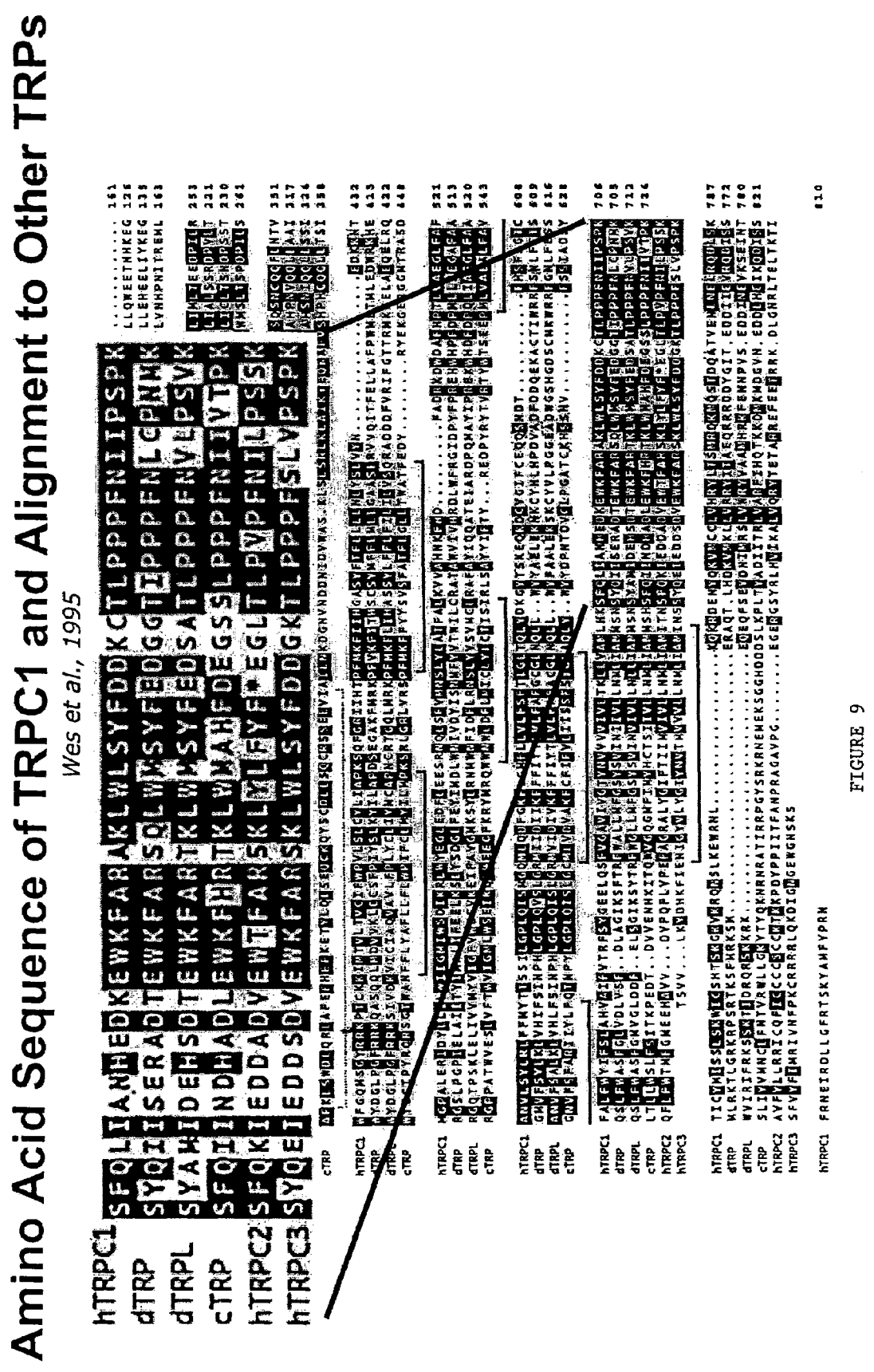

The hypothesis that Homer binds a proline rich sequence in the C-terminus of a family of membrane ion channels termed the Trp channels (Montell et al., 2002; Montell et al., 2002) was examined next. Trp channels are named for the first described member that is the basis for transient receptor potential in *Drosophila* phototransduction (Montell, 2001) and are nonspecific cation channels. This family is now recognized to include Trp channels that mediate influx of extracellular calcium, and VR1 subfamily proteins that mediate pain and temperature sensation (FIG. 8) (Clapham et al., 2001). The sequence LPXPF (SEQ ID NO:23) is conserved in many members of the Trp channel family (FIG. 9) (Montell, 2001), and conforms with the Homer consensus sequence PXXF (SEQ ID NO:3).

Figure 10:
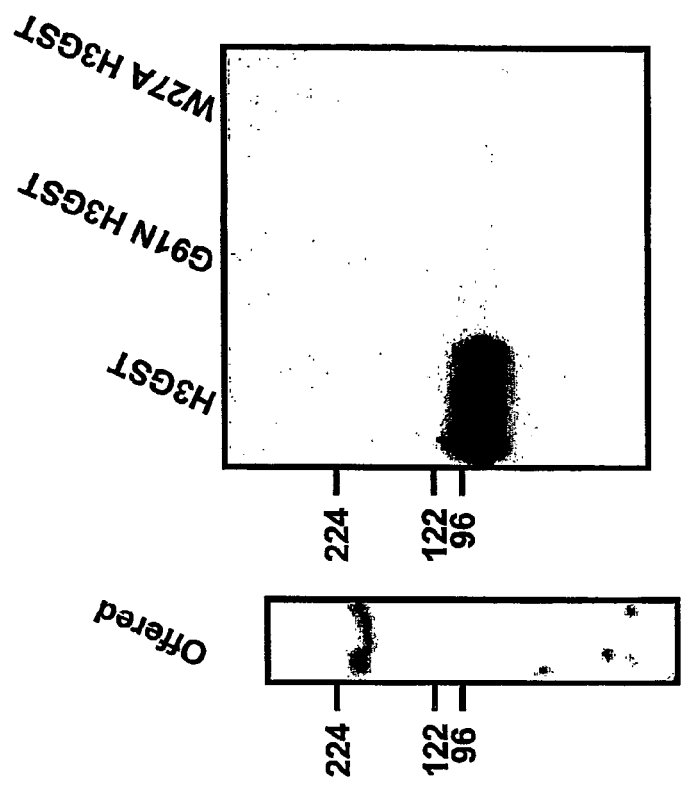
FIG. 10 demonstrates that TrpC1 binds Homer 3. Detergent extracts were prepared from adult rat cerebellum (1% Triton-X100) the soluble lysate was assayed for binding to bead-linked GST-Homer 3 EVH1 or to Homer point mutants G91N or W27A. TrpC1 migrated as a predominant dimer in the lysate. Monomeric TrpC1 bound wild type Homer 3 EVH1 but not point mutant Homers.

To test whether Homer binds TrpC1 channel (Wes et al., 1995), detergent lysates from cerebellum was prepared. TrpC1 is present in cerebellum and migrates on SDS-PAGE as a predominant dimmer species. Lysates were mixed with beads loaded with GST-Homer EVH1 or point mutants (G91N and W27A) that fail to bind mGluR (FIG. 10). The monomer species of TrpC1 binds Homer 3 GST. Binding appears specific since TrpC1 does not bind Homer 1 W24A or Homer 1 G89N. It should be noted that three independent TrpC1 antibodies detect a TrpC1 as a predominant dimer form in tissues. By contrast, the predominant TrpC1 form that binds GST Homer runs as a monomer. These binding data indicate an interaction between Homer and TrpC1 that is dependent on the same sites of interaction as those defined for Homer and mGluR5.

Figure 11:
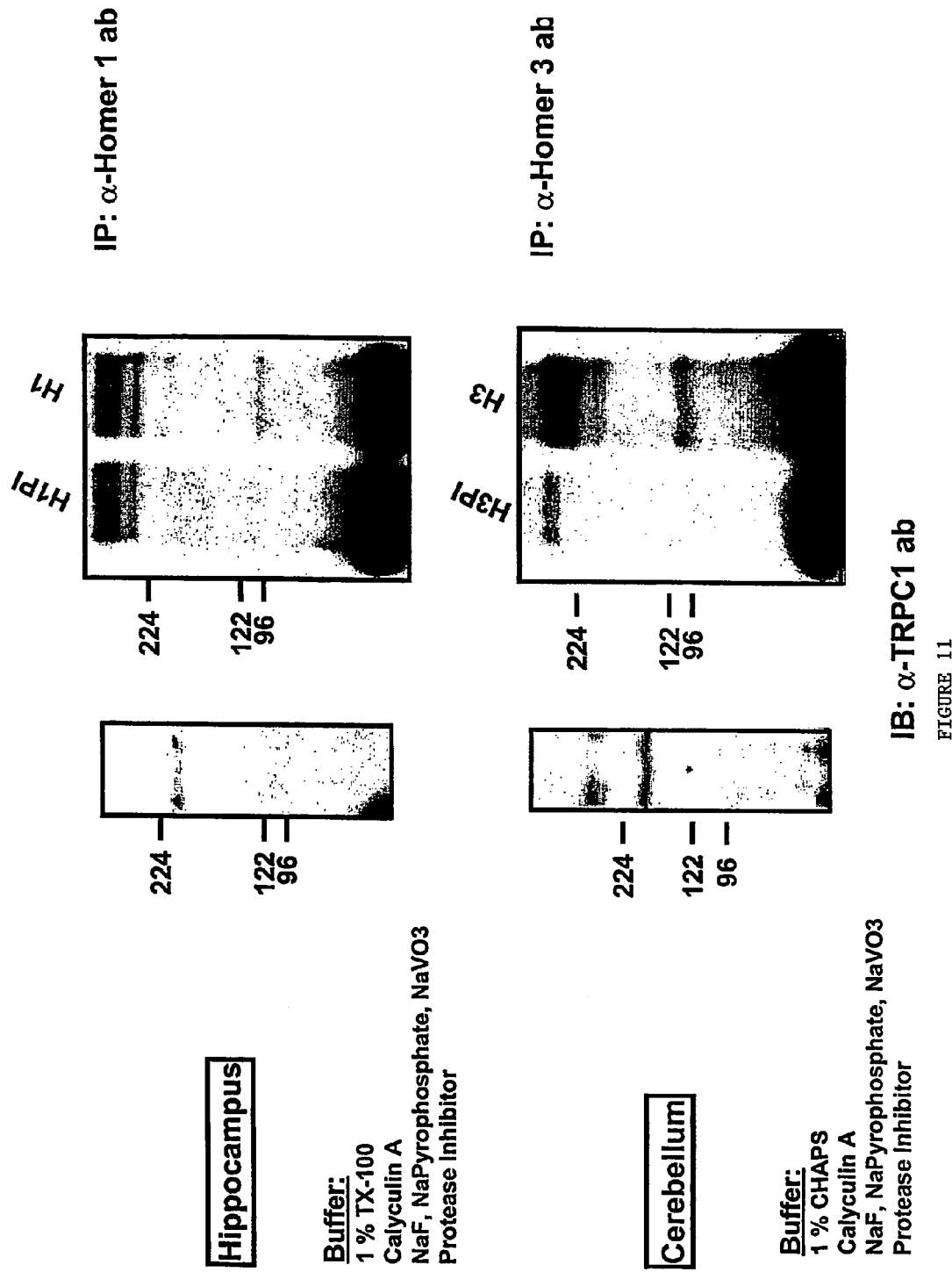
FIG. 11 demonstrates that Trp C1 co-immunoprecipitates with Homer from Adult Rat forebrain and Cerebellum. Soluble detergent lysates were prepared from cerebellum and hippocampus as described in FIG. 10. Immune or preimmune serum was mixed with lyates and associated proteins precipitated with protein G sepharose. Trp C1 monomer form co-IPs with Homer 1 from forebrain and while TrpC1 monomer, and higher molecular weight multimers co-IP with Homer 3 from cerebellum.

To further confirm this interaction, immunoprecipitation studies from rat brain and demonstrated that TrpC1 co-IPs with Homer from hippocampus and cerebellum were performed (FIG. 11). Homer 1 Ab co-IPs the monomer form of TrpC1 from hippocampus, while Homer 3 Ab co-IPs both the monomer and dimer species from cerebellum. Evidence of co-IP from brain indicates that Homer is a natural binding partner with TrpC1.

EXAMPLE 3

Homer Binding to TrpC1 is Dependent on a Proline Rich Sequence in C-terminus

Examination of the molecular specificity of interaction between Homer and TrpC1 was performed. Mutants of TrpC1 were generated and tested for binding to GST-Homer in pull-down assays. Deletion of the C-terminus after the putative Homer binding site did not reduce binding. As predicted from previous studies of Homer EVH1 binding to various other ligands, point mutants of LPPPF (SEQ ID NO:13) to LPPPR (SEQ ID NO:14) resulted in a TrpC1 protein that could not bind Homer (FIG. 12, left). Also consistent with Homer binding specificity to mGluR5 (Tu et al., 1998), mutation to LPLPF (SEQ ID NO:15) did not reduce binding. In contrast to previous mutation analysis of mGluR5, the LLPPF (SEQ ID NO:16) TrpC1 mutant retained binding activity with Homer. In fact, binding to this mutant appeared increased relative to wild type. While this result is not in direct conflict with the proposed molecular understanding of the interaction (Beneken et al., 2000), a similar mutation in mGluR5 substantially reduced binding to Homer (Tu et al., 1998).

EXAMPLE 4

Homer Binds a Novel Ligand in the N-terminus of TrpC1

Further analysis of Homer binding to TrpC1 revealed a second binding site in the N-terminus. During analysis of Homer binding to TrpC1 it was discovered that an N-terminal fragment of TrpC1 also binds Homer. By generating and testing a series of deletion mutants, a second site of interaction was mapped to a sequence present in the N-terminus of TrpC1; LPSSPSSSSP (SEQ ID NO:5). An absence of a phenylalanine in this region was observed, suggesting that the binding interaction may be different from previously described Homer interactions. Mutation of prolines from LPSSPSSSSP (SEQ ID NO:24) to LASSPSSSSP (SEQ ID NO:5) or LPSSASSSSP (SEQ ID NO:17) resulted in TrpC1 mutants that no longer interacted with GST-Homer 3 EVH1 (FIG. 12, right). By contrast, mutation to APSSPSSSSP (SEQ ID NO:18) or LPSSPSSSSA (SEQ ID NO:19) did not reduce binding to Homer. Together, these observations suggest a consensus of PSSP (SEQ ID NO:4).

Figure 13:
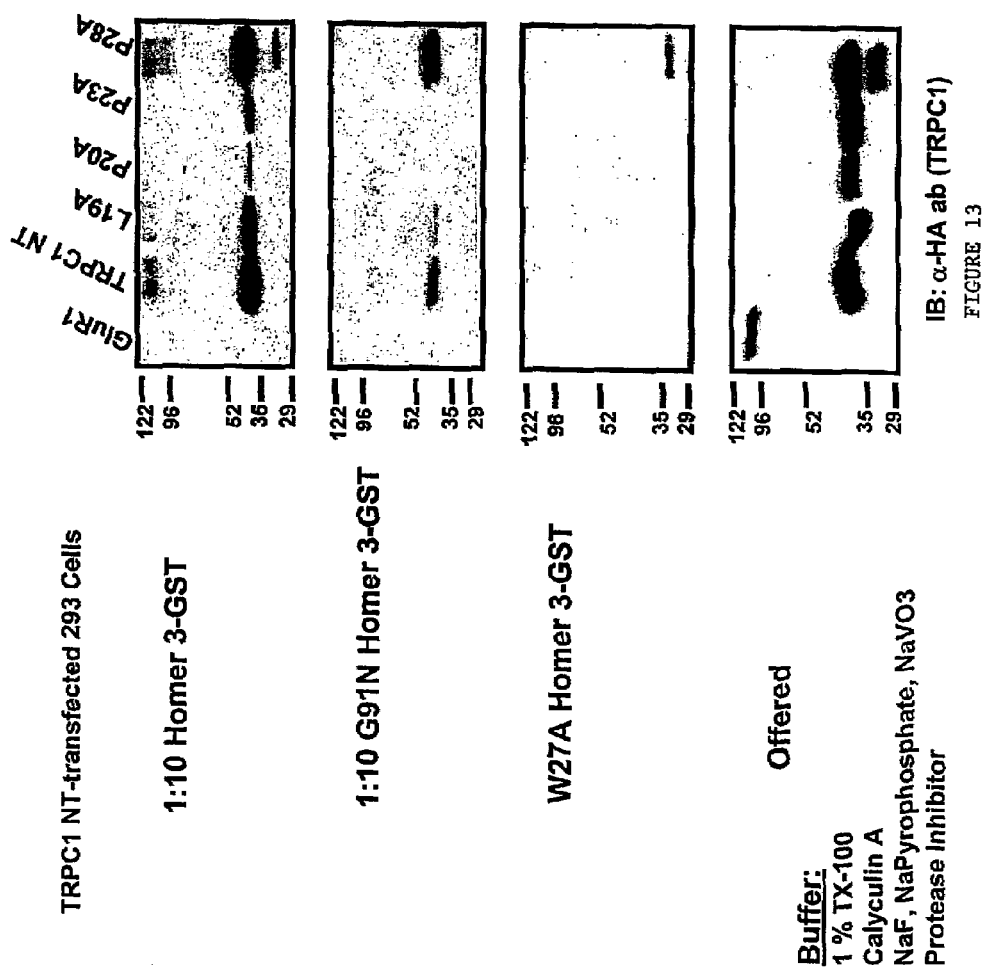
FIG. 13 shows Homer binding to the N-terminus of TrpC1. The N-terminus (~250 aa) of TrpC1 was transiently expressed as either wild type or the indicated point mutant in HEK293 cells and lysates were used for binding to GST Homer 3 or G91N or W27A point mutants of Homer 3. The glutamate receptor GluR1 serves as a negative control for binding. All constructs are tagged with HA. Note that the wt TrpC1 and point mutants show parallel binding to wt Homer and G91N Homer but not to W27A Homer. N-terminal TrpC1 P20A and P23A do not bind Homer.

Consistent with the notion that there is no requirement for a contact with an aromatic hydrocarbon side chain, which is important for conventional Homer binding, it was observed that the N-terminal TrpC1 binds to the G89N mutant of Homer 1 EVH1 (or the equivalent G91N mutant of Homer 3 EVH1, FIG. 13). This binding is less robust than to wt Homer 1 EVH1 but is clearly distinct from the binding observed with proteins that encode conventional Homer ligands (now termed type 1 Homer ligand), which do not bind Homer 1 EVH1G89N (Beneken et al., 2000). Homer binding to the N-terminal sequence (now termed type 2 Homer ligand) does involve the same binding groove as type 1 since the LPSSP (SEQ ID NO:20) ligand does not bind Homer 1 EVH1 W24A mutant. These studies confirmed that Homer binds to two sites in TrpC1. A novel, type 2 Homer ligand (LPSSP, SEQ ID NO:20) is present in the N-terminal sequence and a conventional type 1 Homer ligand (PXXF, SEQ ID NO:3) is present in the C-terminus.

A search of the public data base with the type 2 Homer ligand identifies (among a longer list of genes) the following confirmed Homer interactors: synphilin (Engelender et al., 1999), EF2kinase (Ryazanov et al., 1999; Ryazanov et al., 1997), and Pike (Ye et al., 2002; Ye et al., 2000). Homer has been confirmed to bind each of these proteins using both GST pull down assays and co-immunoprecipitation assays from brain. Another potentially interesting Homer interactor with a type 2 Homer ligand is p70, which is involved in growth factor signaling (Majidi et al., 2000; Majidi et al., 1998), Notch 4 and transcription factors AGIE-BP1 (angiotensinogen gene-reducible enhancer-binding protein 1), cytosolic thymidine kinase, neuronal PAS domain protein 2, zona pellucida sperm-binding protein 3 precursor (sperm receptor), p82 (Majidi et al., 2000), and androgen receptor.

EXAMPLE 5

Homer Binding to TrpC1 is Modified by PPIase Inhibitors

Figure 14:
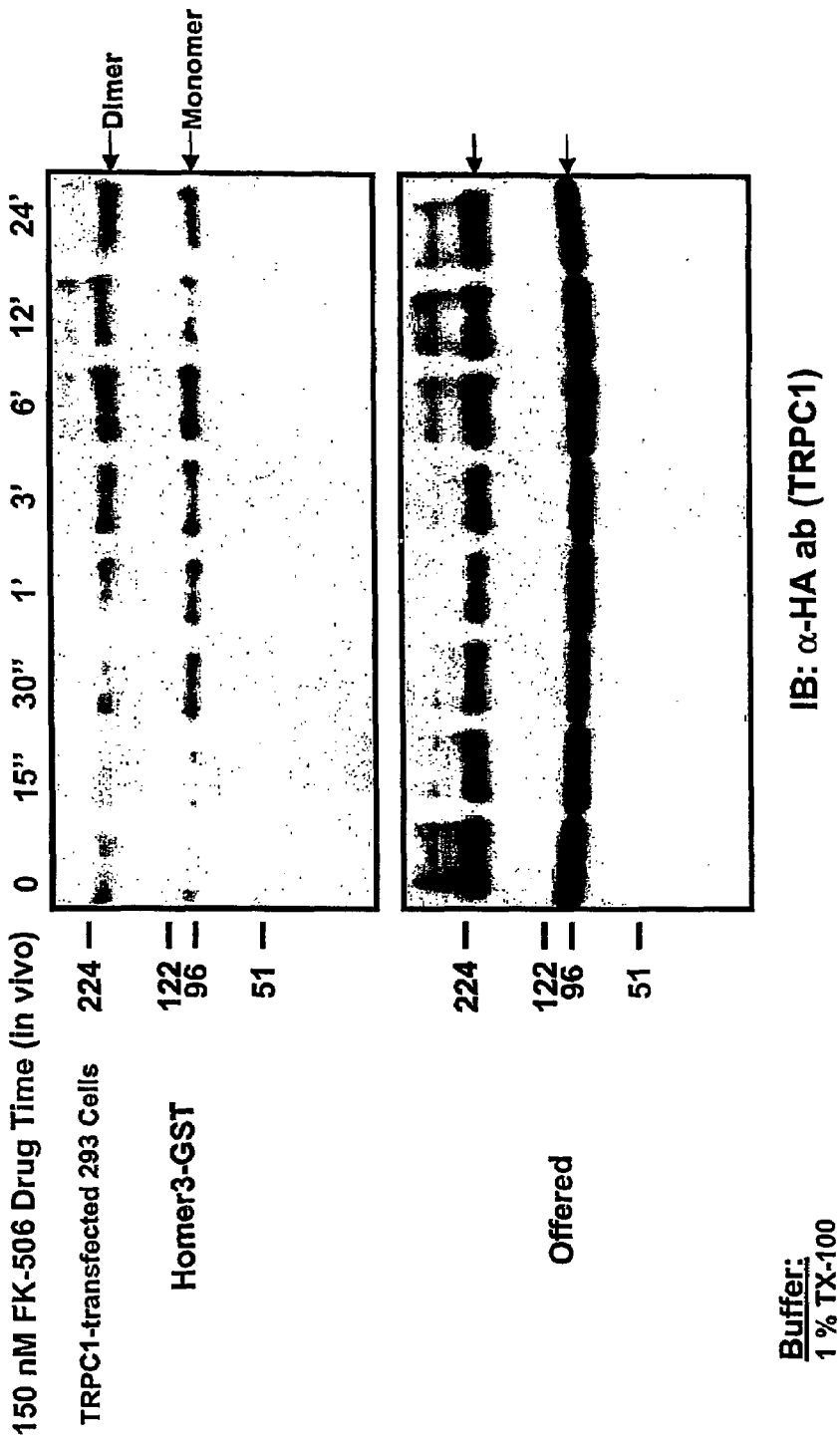
FIG. 14 demonstrates that FK506 increases TrpC1 binding to Homer1EVH1. HEK293 cells that transiently express TrpC1 were treated with FK506 for indicted time prior to preparation of lysates and binding to GST-Homer. Note that FK506 treatment increases TrpC1 binding to Homer.

An observation from the Homer-TrpC1 binding data remained enigmatic. Binding to the N-terminal type 2 Homer ligand is dramatically increased by deletion of the C-terminal site. Additionally, certain point mutants of the C-terminal Homer ligand increase binding to Homer. An answer to this paradox was suggested by a report that showed the *Drosophila* homologue of Trp binds the FKBP protein termed FKBP59 (Goel et al., 2001). The site of interaction was shown to overlap the type 1 Homer ligand in C-terminus of dTrp. The possibility that an FKBP homologue might bind mammalian TrpC1 and impact the binding of Homer was explored. As a first test of this hypothesis, the consequence of treating cells expressing TrpC1 with FK506, and then testing TrpC1 binding to GST-Homer was examined. HEK293 cells were transfected with wt TrpC1 and treated with 150 nM FK506 for times ranging from 15 min to 24 hrs. Cells lysates were prepared in 1% Triton and mixed with GST-Homer1 EVH1 and bound TrpC1 assayed by western blot. Lysates were also assayed to compare expression in each of the samples. FK506 treatment resulted in an increase in the amount of TrpC1 that binds Homer1EVH1 (FIG. 14). This effect was detected as early as 30 min after addition of FK506 and persisted for 24 hrs. A peak of increased binding appeared at ~6hrs. Expression of TrpC1 was not significantly altered during this time course. It was concluded that FK506 increases the binding of TrpC1 to Homer at a dose that is known to the relevant for FKBP.

Figure 15:
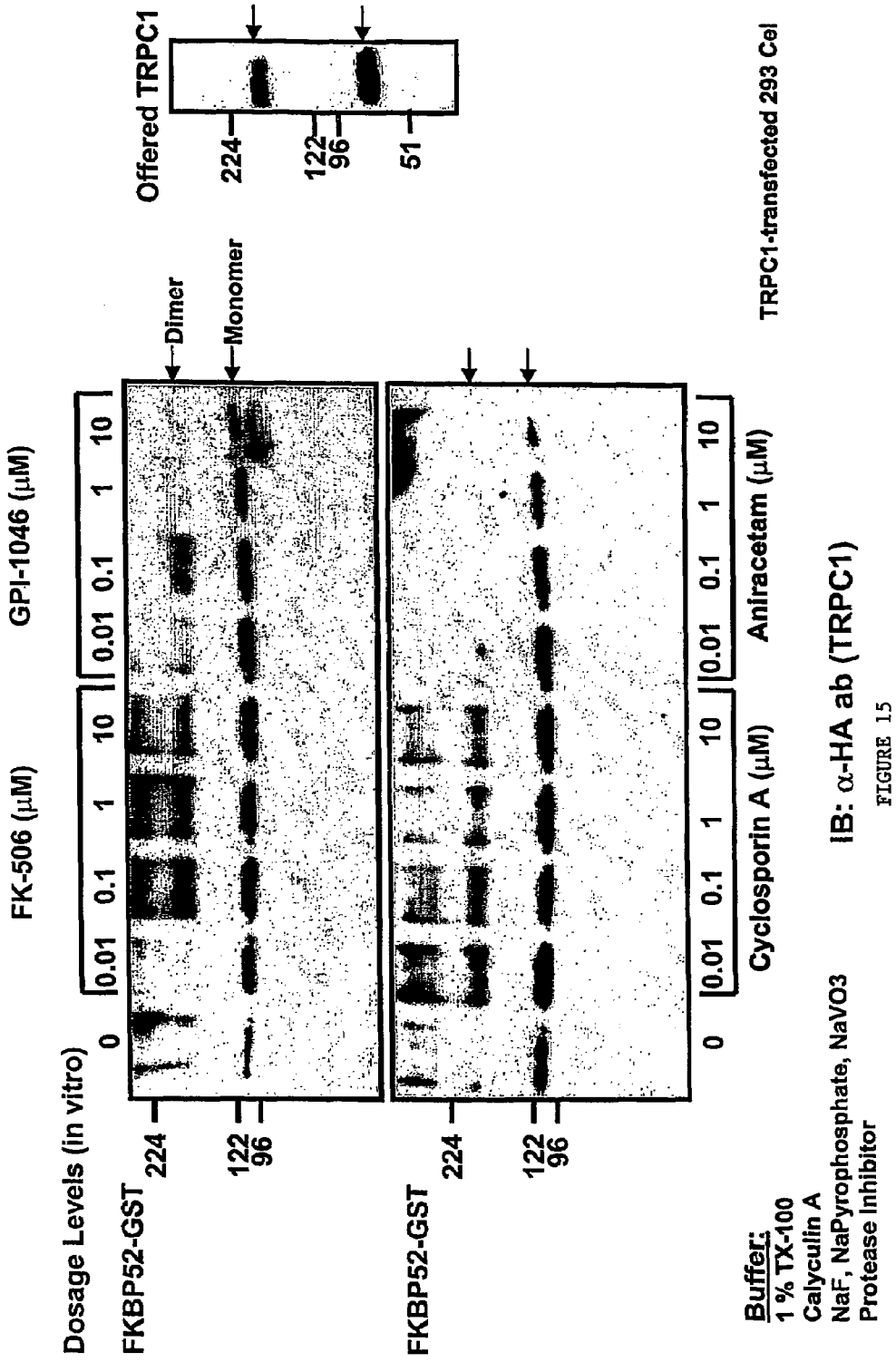
FIG. 15 demonstrates that TrpC1 binds to FKBP52 and this interaction is modified by PPIase inhibitors. TrpC1 was transiently expressed in HEK293 cells and lysates were treated with the indicated concentrations of FK506, GPI1046, cyclosporin A or aniracetam (negative control) and assayed for TrpC1 binding to GSTHomer. TrpC1 migrates as both a monomer and dimer. Note that FK506, GPI1046 and cyclosporin A (but not aniracetam) treatment results in increased TrpC1 binding to Homer.

To further test this hypothesis, the binding of TrpC1 to GST-FKBP12 or GST-FKBP52 was examined. Also, the effect of pretreating cell lysates with FK506, GPI-1046, cyclosporin A or the control agent aniracetam (structurally similar to GPI-1946) was examined. The notion being that dissociation of endogenous FKBP would increase the availability of TrpC1 to bind GST-FKBP in vitro. The FK506 might also be expected to bind to GST-FKBP but because this protein is highly concentrated on the bead and is in vast excess to cellular FKBP, the net consequence of drug treatment would be increased binding of TrpC1 to GST-FKBP. In these assays, TrpC1 bound to FKBP52 (FIG. 15), but not to FKBP12. Binding of TrpC1 to GST-FKBP52 was increased by treatment with both FK506 and GPI1046. The effect of these agents was particularly robust for the dimeric TrpC1 species and was detected with 100 nM FK506 or GPI1046. These studies confirmed that TrpC1 is bound by Homer and FKBP52, and that treatment of cell lysates or cells with drugs that inhibit rotamase activity and dissociate rotamases from their target proteins, result in enhanced binding of TrpC1 to both Homer (FIG. 14) and FKBP52 (FIG. 15).

Control experiments examined the possibility that Homer binding might be directly modified by FK506. A synthetic peptide that includes the Homer ligand site of mGluR5 was linked to bovine serum albumin (BSA) and this protein complex was linked to Affigel (Biorad). Purified recombinant Homer 1 was treated with 50 micromolar FK506 and its binding to the synthetic peptide assayed. As anticipated, Homer 1 binds to the mGluR5 peptide. Binding was not affected by pretreatment with FK506. It was concluded that Homer binding to type 1 Homer ligand is not altered by FK506.

EXAMPLE 6

Homer Binding to TrpC1 is Inhibited by Co-expressed FKBP12 or FKBP52

Figure 16:
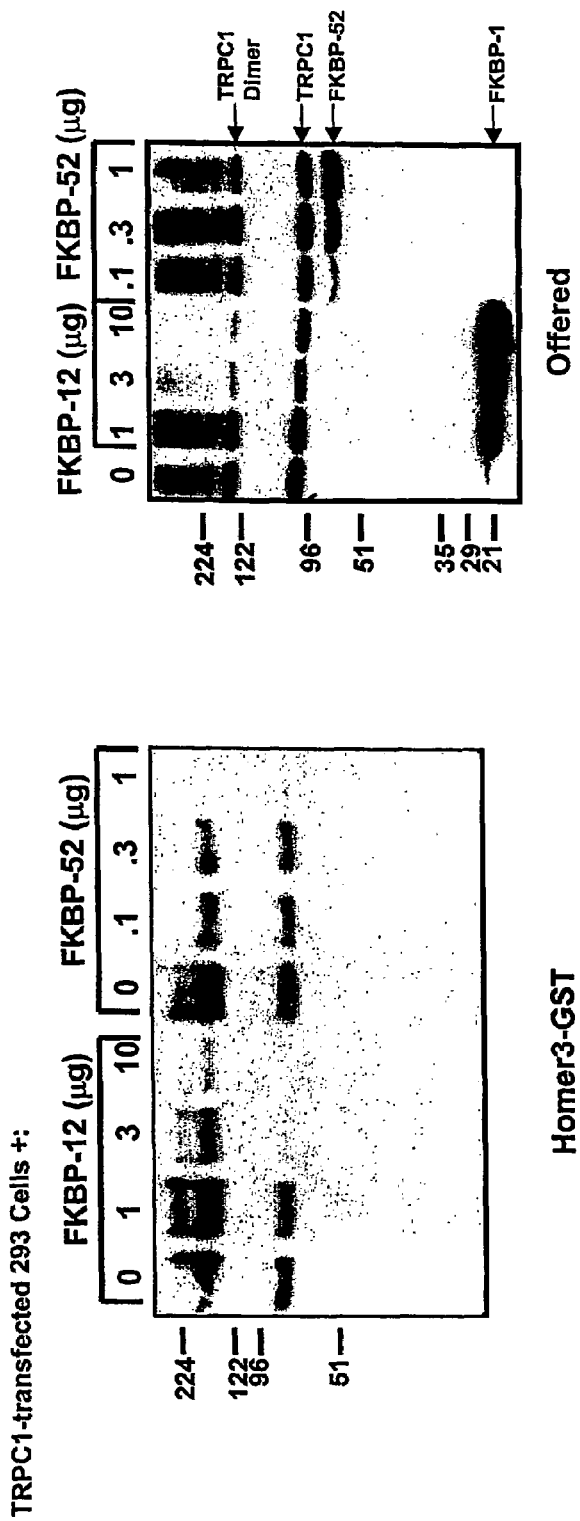
FIG. 16 demonstrates that Homer Binding to TrpC1 is inhibited by co-expressed FKBP12 or FKBP52. TrpC1 and either FKBP12 or FKBP52 were transiently expressed in HEK293 cells and lysates assayed for binding to GST-Homer. FKBP12 or FKBP52 inhibited the binding of TrpC1 to Homer but did not substantially affect expression of TrpC1 in lyates.

To test the hypothesis that FKBPs can compete for Homer binding, cells were co-transfected with TrpC1 and either FKBP12 or FKBP52 and GST-Homer binding assays were performed. In these assays, FKBP12 or FKBP52 inhibited the binding of TrpC1 to Homer (FIG. 16).

EXAMPLE 7

Binding of Synaptic Activation Protein Homer Protein to mGluR5

Hippocampal lysate was prepared by sonicating hippocampi of 21 day old rats (3×10 seconds) in PBS and 1% Triton with protease inhibitors, centrifuging for 10 minutes at 15,000 g, and preclearing with CL-4B sepharose beads (Pharmacia, Piscataway, N.J.). Homer affinity columns were prepared by irreversibly crosslinking Homer GST fusion protein to Affigel agarose beads (1 mg Homer protein per 1 ml bed volume; Bio-Rad Laboratories, Richmond, Calif.). 40 ml of beads were then incubated with lysate from one hippocampus for one hour at 4° C., washed three times with PBS, and bound mGluR5 was eluted by boiling in 3× loading buffer.

For experiments examining specificity of Homer binding to metabotropic glutamate receptors, HEK293 cells were transiently transfected with mGluR1α, mGluR2, mGluR4 or mGluR5 expression constructs, scraped into PBS+1% Triton X100, sonicated 2×10 seconds, centrifuged at 15,000 g for 10 minutes at 4° C., and pre-cleared. Lysate from half of a 10 cm plate was incubated with 50 µl of beads linked to 250 ng of protein and washed as above. Samples were analyzed by western blot analysis using the appropriate polyclonal mGluR antibody. Deletion constructs of Homer were prepared by PCR and cloned as fusion constructs with GST in pGEX (Pharmacia, Piscataway, N.J.).

Hippocampal lysate was prepared as above. Rabbit anti-Homer serum or pre-immune serum were irreversibly linked to "AFFIGEL" agarose beads (Bio-Rad Laboratories, Richmond, Calif.) and washed extensively with PBS. 50 µl beads were incubated with lysate from one hippocampus overnight at 4° C., washed 2× with PBS with 1% Triton and 2× with PBS, resuspended in 3× SDS loading buffer and analyzed by gel electrophoresis and western blot analysis. In control experiments, co-immunoprecipitation of mGluR5 was blocked by pre-incubating anti-Homer linked beads with 50 µg of Homer GST-fusion protein for 1 hour at 4° C.

EXAMPLE 8

Effect of FK-506 on Homer-mGluR1 Interaction In Vivo

Figure 17:
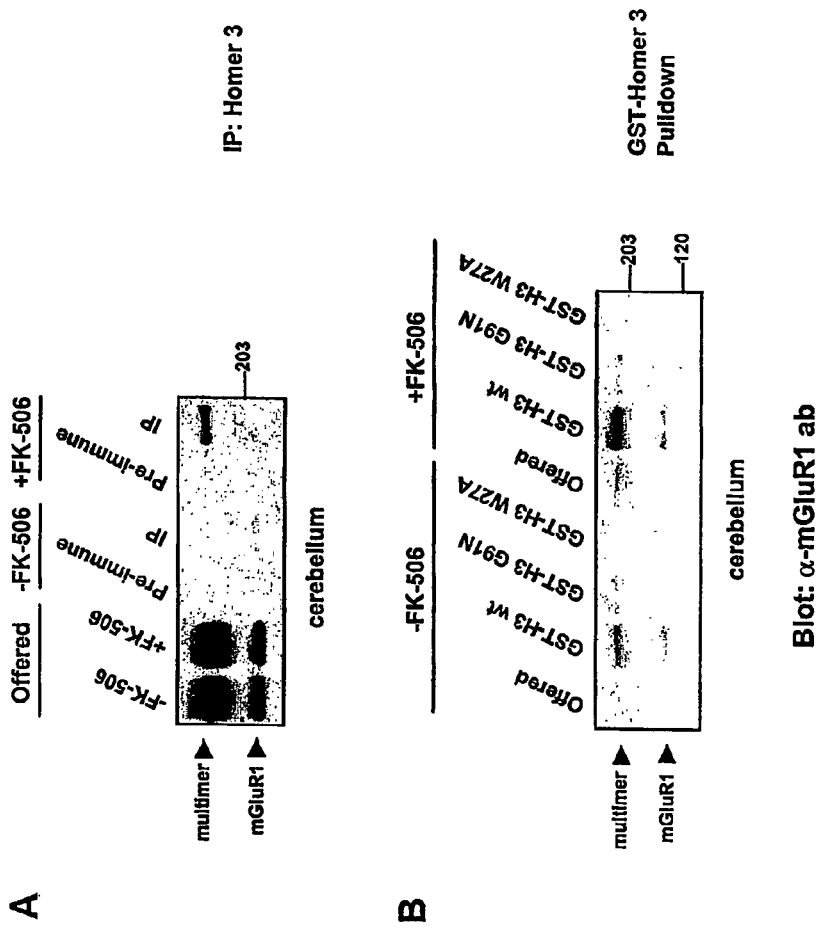
FIG. 17 shows that Homer binding to mGluR1 is increases with the addition of FK-506 in vivo in Rats. Rats were injected with FK-506 and subsequently sacrificed where the cerebellum was collected. (A) Homer 3 co-precipitation of mGluR1. (B) WT GST Homer-3 co-immunoprecipitation of mGluR1.

To test the effect of PPIase inhibitors on Homer binding in vivo, adult rats were injected (i.p.) with 10 mg/kg of FK-506 or vehicle (DMSO) only. After 3 hours, the rats were sacrificed, and the cerebellum was collected. The results indicated that Homer binding to mGluR1 increased with FK-506 versus control (FIG. 17).

Although the invention has been described with reference to the above examples, it will be understood that modifications and variations are encompassed within the spirit and scope of the invention. Accordingly, the invention is limited only by the following claims.

REFERENCES

Beneken, J., Tu, J. C., Xiao, B., Nuriya, M., Yuan, J. P., Worley, P. F., and Leahy, D. J. (2000). Structure of the Homer EVH1 domain-peptide complex reveals a new twist in polyproline recognition. Neuron 26, 143-54.

Brakeman, P. R., Lanahan, A. A., O'Brien, R., Roche, K., Barnes, C. A., Huganir, R. L., and Worley, P. F. (1997). Homer: a protein that selectively binds metabotropic glutamate receptors. Nature 386, 284-8.

Clapham, D. E., Runnels, L. W., and Strubing, C. (2001). The TRP ion channel family. Nat Rev Neurosci 2, 387-96.

Engelender, S., Kaminsky, Z., Guo, X., Sharp, A. H., Amaravi, R. K., Kleiderlein, J. J., Margolis, R. L., Troncoso, J. C., Lanahan, A. A., Worley, P. F., Dawson, V. L., Dawson, T. M., and Ross, C. A. (1999). Synphilin-1 associates with alpha-synuclein and promotes the formation of cytosolic inclusions. Nat Genet 22, 110-4.

Feng, W., Tu, J., Yang, T., Shih Vernon, P., Allen, P. D., Worley, P. F., and Pessah, I. N. Homer (2002) Regulates Gain of Ryanodine Receptor Channel Complex. J Biol Chem 277, 44722-30.

Goel, M., Garcia, R., Estacion, M., and Schilling, W. P. (2001). Regulation of *Drosophila* TRPL channels by immunophilin FKBP59. J Biol Chem 276, 38762-73.

Gold, B. G., and Nutt, J. G. (2002). Neuroimmunophilin ligands in the treatment of Parkinson's disease. Curr Opin Pharmacol 2, 82-6.

Gothel, S. F., and Marahiel, M. A. (1999). Peptidyl-prolyl cis-trans isomerases, a superfamily of ubiquitous folding catalysts. Cell Mol Life Sci 55, 423-36.

Guo, X., Dillman, J. F., 3rd, Dawson, V. L., and Dawson, T. M. (2001). Neuroimmunophilins: novel neuroprotective and neuroregenerative targets. Ann Neurol 50, 6-16.

Kammermeier, P. J., Xiao, B., Tu, J. C., Worley, P. F., and Ikeda, S. R. (2000). Homer proteins regulate coupling of group I metabotropic glutamate receptors to N-type calcium and M-type potassium channels [In Process Citation]. J Neurosci 20, 7238-45.

Lu, K. P. (2000). Phosphorylation-dependent prolyl isomerization: a novel cell cycle regulatory mechanism. Prog Cell Cycle Res 4, 83-96.

Lu, K. P., Hanes, S. D., and Hunter, T. (1996). A human peptidyl-prolyl isomerase essential for regulation of mitosis. Nature 380, 544-7.

Majidi, M., Gutkind, J. S., and Lichy, J. H. (2000). Deletion of the COOH terminus converts the ST5 p70 protein from an inhibitor of RAS signaling to an activator with transforming activity in NIH-3T3 cells. J Biol Chem 275, 6560-5.

Majidi, M., Hubbs, A. E., and Lichy, J. H. (1998). Activation of extracellular signal-regulated kinase 2 by a novel Abl-binding protein, ST5. J Biol Chem 273, 16608-14.

Montell, C. (2001). Physiology, phylogeny, and functions of the TRP superfamily of cation channels. Sci STKE 2001, RE1.

Montell, C., Birnbaumer, L., and Flockerzi, V. (2002). The TRP Channels, a Remarkably Functional Family. Cell 108, 595-8.

Montell, C., Birnbaumer, L., Flockerzi, V., Bindels, R. J., Bruford, E. A., Caterina, M. J., Clapham, D. E., Harteneck, C., Heller, S., Julius, D., Kojima, I., Mori, Y., Penner, R., Prawitt, D., Scharenberg, A. M., Schultz, G., Shimizu, N., and Zhu, M. X. (2002). A unified nomenclature for the superfamily of TRP cation channels. Mol Cell 9, 229-31.

Ryazanov, A. G., Pavur, K. S., and Dorovkov, M. V. (1999). Alpha-kinases: a new class of protein kinases with a novel catalytic domain. Curr Biol 9, R43-5.

Ryazanov, A. G., Ward, M. D., Mendola, C. E., Pavur, K. S., Dorovkov, M. V., Wiedmann, M., Erdjument-Bromage, H., Tempst, P., Parmer, T. G., Prostko, C. R., Germino, F. J., and Hait, W. N. (1997). Identification of a new class of protein kinases represented by eukaryotic elongation factor-2 kinase. Proc Natl Acad Sci USA 94, 4884-9.

Schiene, C., and Fischer, G. (2000). Enzymes that catalyse the restructuring of proteins. Curr Opin Struct Biol 10, 40-5.

Snyder, S. H., Lai, M. M., and Burnett, P. E. (1998). Immunophilins in the nervous system. Neuron 21, 283-94.

Snyder, S. H., Sabatini, D. M., Lai, M. M., Steiner, J. P., Hamilton, G. S., and Suzdak, P. D. (1998). Neural actions of immunophilin ligands. Trends Pharmacol Sci 19, 21-6.

Steiner, J. P., Connolly, M. A., Valentine, H. L., Hamilton, G. S., Dawson, T. M., Hester, L., and Snyder, S. H. (1997). Neurotrophic actions of nonimmunosuppressive analogues of immunosuppressive drugs FK506, rapamycin and cyclosporin A. Nat Med 3, 421-8.

Tu, J. C., Bo Xiao, B., Naisbitt, S., Yuan, J. P., Petralia, R. S., Brakeman, P. R., Aakalu, V. K., Lanahan, A. A., Sheng, M., and Worley, P. (1999). mGluR/Homer and PSD-95 Complexes Are Linked by the Shank Family of Postsynaptic Density Proteins. Neuron 23, 583-592.

Tu, J. C., Xiao, B., Yuan, J., Lanahan, A., Leoffert, K., Li, M., Linden, D., and Worley, P. F. (1998). Homer binds a novel proline rich motif and links group1 metabotropic glutamate receptors with IP3 receptors. Neuron 21, 717-726.

Wes, P. D., Chevesich, J., Jeromin, A., Rosenberg, C., Stetten, G., and Montell, C. (1995). TRPC1, a human homolog of a *Drosophila* store-operated channel. Proc Natl Acad Sci USA 92, 9652-6.

Xiao, B., Tu, J. C., Petralia, R. S., Yuan, J., Doan, A., Breder, C., Ruggiero, A., Lanahan, A. A., Wenthold, R. J., and Worley, P. F. (1998). Homer regulates the association of Group 1 metabotropic receptors with multivalent complexes of Homer-related, synaptic proteins. Neuron 21, 707-716.

Xiao, B., Tu, J. C., and Worley, P. F. (2000). Homer: a link between neural activity and glutamate receptor function. Curr Opin Neurobiol 10, 370-4.

Ye, K., Aghdasi, B., Luo, H. R, Moriarity, J. L., Wu, F. Y., Hong, J. J., Hurt, K. J., Bae, S. S., Suh, P. G., and Snyder, S. H. (2002). Phospholipase C gamma 1 is a physiological guanine nucleotide exchange factor for the nuclear GTPase PIKE. Nature 415, 541-4.

Ye, K., Hurt, K. J., Wu, F. Y., Fang, M., Luo, H. R., Hong, J. J., Blackshaw, S., Ferris, C. D., and Snyder, S. H. (2000). Pike. A nuclear gtpase that enhances PI3kinase activity and is regulated by protein 4.1N. Cell 103, 919-30.

What is claimed is:

1. A method of screening for activity of modulating agents of a Homer signaling pathway comprising:
   i) contacting at least one protein or peptide having a proline-type Homer ligand consensus sequence in the presence of a peptidylproline cis-trans isomerase (PPIase) inhibitor with at least one test agent for a sufficient time to allow the components to interact;
   ii) contacting the components of step (i) with a Homer protein;
   iii) determining whether binding between the at least one protein or peptide and Homer protein is increased or decreased as compared to the binding in the absence of the test agent, wherein increased or decreased binding between the at least one protein or peptide and Homer protein is indicative of a modulating agent for a Homer signaling pathway.

2. The method of claim 1, wherein as the concentration of the at least one agent increases, decreasing binding of Homer protein to the at least one protein or peptide is indicative of the presence of a competitive Homer ligand.

3. The method of claim 1, wherein step iii) further comprises immunoprecipitation of a complex between the Homer protein and the at least one protein or peptide.

4. The method of claim 1, wherein the PPIase inhibitor shows a biphasic effect at separate concentrations.

5. The method of claim 4, further wherein the PPIase inhibitor is present in at least two concentrations, wherein one concentration of the inhibitor does not inhibit Homer binding to the at least one protein or peptide and another concentration of inhibitor inhibits Homer binding to the at least one protein or peptide.

6. The method of claim 5, wherein modulation of Homer protein binding by the agent at the concentration of PPIase inhibitor which does not inhibit binding of the Homer protein is indicative of the presence of a modulating agent of a Homer signaling pathway.

7. The method of claim 1, wherein the PPIase inhibitor is a rotamase inhibitor.

8. The method of claim 1, wherein the PPIase inhibitor is selected from the group consisting of FK506, cyclosporin A, and GPI-1046.

9. The method of claim 8, wherein the PPIase inhibitor is GPI-1046.

10. The method of claim 1, wherein binding between the at least one protein or peptide and Homer protein is determined by an endpoint assay selected from the group consisting of modulation of $Ca^{+2}$ signaling, modulation of PLC, modulation of Trp channels, modulation of MAP kinase, modulation of PBkinase, modulation of ion channels, modulation of IP3 channels, modulation of RYR channels, and modulation of growth factor dependent responses.

11. The method of claim 1, wherein the at least one protein or peptide and Homer protein are in a cell or cell lysate.

12. The method of claim 11, wherein the at least one protein or peptide and Homer proteins are in a cell.

13. The method of claim 12, wherein the cell is a transformed cell.

14. The method of claim 13, wherein the at least one protein or peptide or the Homer protein is a recombinant peptide or protein.

15. The method of claim 14, wherein the recombinant at least one protein or peptide is set forth in SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, SEQ ID NO:52, or SEQ ID NO:53.

16. The method of claim 15, wherein the sequence is set forth in SEQ ID NO:31.

17. The method of claim 1, wherein the Homer ligand consensus sequence is a proline-type 1 Homer ligand consensus sequence or a proline-type 2 Homer ligand consensus sequence.

18. The method of claim 17, wherein the proline-type Homer ligand consensus sequence is set forth in SEQ ID NO: 4.

19. The method of claim 1, wherein the at least one protein or peptide is a synthetic oligopeptide comprising at least 4 amino acid residues, but not more than 10 amino acid residues, having the consensus sequence as set forth in SEQ ID NO: 4.

20. The method of claim 19, wherein the synthetic oligopeptide is set forth in SEQ ID NO:5.

21. The method of claim 1, wherein the at least one protein or peptide is selected from a protein in the group consisting of synphilin, EF2kinase, p70, Notch 4, AGIE-BP1, cytosolic thymidine kinase, neuronal PAS domain protein 2, zona pellucida sperm binding protein 3 precursor, Shank family of proteins, ryanodine receptor (RYR), p82, androgen receptor, TrpC1, mGluRla and mGluR5.

22. The method of claim 1, wherein the PPIase is selected from the group consisting of FKBP family, cyclophilin family, and Pin family of PPIases.

23. The method of claim 1, wherein the PPIase is FKBP 52 or FKBP 12.

24. The method of claim 23, wherein the PPIase is FKBP52.

25. The method of claim 1, wherein the Homer protein is a human protein.

26. The method of claim 1, wherein the Homer protein is selected from the group of consisting of SEQ ID NO:54, SEQ ID NO:55, SEQ ID NO:56, SEQ ID NO:57, and SEQ ID NO:58.

27. The method of claim 1, wherein the Homer protein is set forth in SEQ ID NO: 7.

28. The method of claim 1, wherein the test agent that affects the Homer signaling pathway is selected from a neuroprotective agent or an immunosuppressive agent.

29. The method of claim 28, wherein the Homer signaling pathway is associated with a disorder selected from the group consisting of peripheral neuropathies and neurological pathologies related to neurodegeneration.

30. The method of claim 29, wherein the disorder is selected from the group consisting of psoriasis, inflammatory bowel disease, adult respiratory distress syndrome, dermatitis, meningitis, encephalitis, eczema, asthma, skin hypersensitivity reactions, atherosclerosis, leukocyte adhesion deficiency, rheumatoid arthritis, systemic lupus erythematosus (SLE), diabetes mellitus, multiple sclerosis, Reynaud's syndrome, autoimmune thyroiditis, experimental autoimmune encephalomyelitis, Sjorgen's syndrome, juvenile onset diabetes, tuberculosis, sarcoidosis, polymyositis, granulomatosis, vasculitis, pernicious anemia, diseases involving leukocyte diapedesis, CNS inflammatory disorder, multiple organ injury syndrome secondary to septicemia or trauma, autoimmune hemolytic anemia, myasthenia gravis, antigen-antibody complex mediated diseases, and transplantations, including graft versus host or host versus graft disease.

* * * * *